United States Patent
Namba et al.

(10) Patent No.: US 9,222,016 B2
(45) Date of Patent: Dec. 29, 2015

(54) COMPOUND HAVING FLUORESCENT CHROMOPHORE, ION CONCENTRATION SENSOR INCLUDING COMPOUND, REAGENT INCLUDING COMPOUND, REAGENT KIT PROVIDED WITH REAGENT, PRECURSOR OF COMPOUND, AND METHOD FOR SYNTHESIZING COMPOUND

(75) Inventors: Kosuke Namba, Sapporo (JP); Ayumi Osawa, Sapporo (JP); Keiji Tanino, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 14/004,387

(22) PCT Filed: Mar. 8, 2012

(86) PCT No.: PCT/JP2012/056040
§ 371 (c)(1),
(2), (4) Date: Sep. 10, 2013

(87) PCT Pub. No.: WO2012/121356
PCT Pub. Date: Sep. 13, 2012

(65) Prior Publication Data
US 2014/0005410 A1    Jan. 2, 2014

(30) Foreign Application Priority Data
Mar. 10, 2011   (JP) .................................. 2011-053009

(51) Int. Cl.
C07D 209/58    (2006.01)
C09K 11/06    (2006.01)
C07D 487/04    (2006.01)
C09B 57/00    (2006.01)
C09K 9/02    (2006.01)
C07D 249/16    (2006.01)

(52) U.S. Cl.
CPC .............. *C09K 11/06* (2013.01); *C07D 487/04* (2013.01); *C09B 57/00* (2013.01); *C09K 9/02* (2013.01); *C07D 249/16* (2013.01); *C09K 2211/1007* (2013.01); *C09K 2211/1059* (2013.01)

(58) Field of Classification Search
CPC ............................ C07D 249/04; C07D 249/16
USPC ......................................................... 548/258
See application file for complete search history.

(56) References Cited

U.S. PATENT DOCUMENTS 3,262,944 A * 7/1966 Harder et al. .................. 548/258

FOREIGN PATENT DOCUMENTS

JP      2003-068464      3/2003

OTHER PUBLICATIONS

Extended European Search Report in corresponding application EP12755329, Jul. 21, 2014.
Koga H et al. "Mesoionic 1,3a,6a-triazapentalenes" Tetrahedron Letters 15:1291-1294, 1978.
Albini A et al. "Singlet oxygen photo-oxidation of some triazapentalenes" J.C.S. Perkin I, pp. 2904-2908, 1980.
Albini A et al. "Heteropentalenes. On 5H-pyrazolo[1',2':1,2]1,2,3-triazolo[5,4-a]-phenazinyliumide" J.C.S. Perkin I, pp. 1821-1825, 1981.
Albini et al. "Chemistry of Nitrenes Generated by the Photocleavage of Both Azides and a Five-Membered Heterocycle." J. Amer. Chem. Soc. 113, 6928-6934, 1991.
Falchi et al. "Fluorescence of Antiaromatic Systems: An Experimental and Theoretical Study of 1,3,5-Tri-tert-butylpentalene." J. Phys. Chem. A 1998, 102, 5006-5012.
Gerard et al. "Synthesis of 1,4,5-trisubstituted-1,2,3-triazoles by copper-catalyzed cycloaddition-coupling of azides and terminal alkynes." Tetrahedron 62 (2006) 6405-6411.
Koga et al. "Mesoionic 1,3a,6a-Triazapentalenes." Tetrahedron Letters No. 15, pp. 1291-1294, 1978.
Lee et al. "New Routes to 1,2-Diazoles with a Fused Ring System by Reductive and Oxidative Cyclizations." Chemistry Letters, pp. 951-954, 1974.
McRobbie et al. "Competitive Cyclisations of Singlet and Triplet Nitrenes. Part I. Cyclisation of 1-(2-Nitrenophenyl) Pyrazoles." Tetrahedron Letters No. 12, pp. 925-928, 1976.
Namba et al. "Direct Synthesis of Fluorescent 1,3a,6a-Triazapentalene Derivatives via Click-Cyclization-Aromatization Cascade Reaction." Journal of the American Chemical Society 2011, 133, 11466-11469.
Tsuge et al. "Studies of Polyazapentalenes. III. Electrophilic Reactions of 8-Substituted Dibenzo [b,e]-1,3a,6a-Triazapentalene." Chemistry Letters, pp. 175-1880, 1973.

(Continued)

*Primary Examiner* — Joseph Kosack
*Assistant Examiner* — Karen Cheng
(74) *Attorney, Agent, or Firm* — K&L Gates LLP; Louis C. Cullman; Michelle Glasky Bergman

(57) ABSTRACT

A compound of the present invention comprises a triazapentalene backbone represented by the general formula 1 below as a fluorescent chromophore.

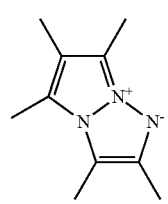

9 Claims, 14 Drawing Sheets

(56) References Cited

OTHER PUBLICATIONS

Cai, R. et al., Facile synthesis of fluorescent active triazapentalenes through gold-catalyzed triazole-alkyne cyclization, 50 CHEM. COMM. 7303 (2014).

March, J., Advanced Organic Chemistry 280, (4th ed. 1992).
Namba, K. et al., Synthesis of yellow and red fluorescent 1,3a,6atriazapentalenes and the theoretical investigation of their optical properties, 6 CHEM. SCI. 1083 (2015).
Carey, Francis A. & Richard J. Sundberg, Advanced Organic Chemistry 201 (3rd ed. 1993).

* cited by examiner

COMPOUND HAVING FLUORESCENT CHROMOPHORE, ION CONCENTRATION SENSOR INCLUDING COMPOUND, REAGENT INCLUDING COMPOUND, REAGENT KIT PROVIDED WITH REAGENT, PRECURSOR OF COMPOUND, AND METHOD FOR SYNTHESIZING COMPOUND

CROSS REFERENCE TO RELATED APPLICATIONS

The present application is a national phase of PCT/JP2012/056040 filed on Mar. 8, 2012, which claims priority to Japanese Patent Application 2011-053009 filed on Mar. 10, 2011, the entire disclosures of which are incorporated by reference herein.

TECHNICAL FIELD

The present invention relates to a compound having a fluorescent chromophore, an ion concentration sensor comprising the compound, a reagent comprising the compound, a reagent kit provided with the reagent, a precursor of the compound, and a method for synthesizing the compound.

BACKGROUND ART

Fluorescent molecules are widely used in various areas of studies and industries including luminescent materials such as an organic EL device, living organisms-related basic research employing bioimaging, and scenes of medical diagnosis; and are important class of compounds supporting the foundation of modern technology.

The fluorescent molecule is required to have various characteristics and functions in accordance with an application thereof. Thus, creation of fluorescent compounds having novel characteristics or functions is considered to be always necessary. Development of these fluorescent molecules strongly promotes growth of various basic research and industries.

A number of fluorescent molecules have been developed thus far; and various derivative such as coumalin or acridine, and the like have been used. Further, TAMRA (CAS registry number: 150322-06-8) or the like is used in living organisms-related basic research or the like.

Further, Salvi and others have reported that 1,3,5-tri-tert-butylpentalene which is a kind of pentalene is a fluorescent molecule (Non Patent Literature 1).

CITATION LIST

Patent Literature

Patent Literature 1: Unexamined Japanese Patent Application Kokai Publication No. 2003-68464.

Non Patent Literature

Non Patent Literature 1: A. Falchi, C. Gellini, P. R. Salvi. J. Phys. Chem. 1998, 102, 5006-5012.
Non Patent Literature 2: H. Koga, M. Hirobe, T. Okamoto. Tetrahedron Lett. 1978, No. 15, pp. 1291-1294.
Non Patent Literature 3: O. Tsuge, H. Samura. Chem. Lett. 1973, pp. 175-180.
Non Patent Literature 4: J. H. Lee, A. Matsumoto, M. Yoshida, O. Shimomura Chem. Lett. 1974, pp. 951-954.
Non Patent Literature 5: I. M. McRobbie, O. Meth-Cohn, H. Suschitzky. Tetrahedron Lett. 1976, No. 12, pp. 925-928.

SUMMARY OF INVENTION

Technical Problem

Although a number of fluorescent molecules have been thus far developed and used in various fields, existing fluorescent molecules have the following problems.

In order to function as a fluorescent molecule, the molecule needs to have an extended π conjugated system; and an aromatic functional group is often introduced therein. Because of this, many molecules are very large (long) in size and poorly water-soluble. On the other hand, in order to apply to living organisms-related basic research or a reagent for water quality survey, fluorescent molecules with high water-solubility have been desired.

Although there are compact fluorescent molecules, the quantum yield of such fluorescent molecules is not adequate. On the other hand, for expansion to living organisms-related basic research including a cellular uptake experiment or medical diagnosis, development of fluorescent molecules that have a high quantum yield in spite of being a compact molecule has been desired. Further, there have been some cases where a solvent is restricted when the existing fluorescent molecule is introduced in various bioactive compounds or functional compounds. Furthermore, molecular design for producing a molecule having expected absorption fluorescence wavelength was not easy.

Pentalene has a compact backbone but is an anti-aromatic compound with an 8π electron system and known to be a very unstable compound. Synthesis thereof was often difficult. A fluorescent molecule that is synthesizable in a simple and prompt fashion was needed.

For example, 1,3,5-tri-tert-butylpentalene described in Non Patent Literature 1 is synthesized by introducing three sterically-bulky tert-butyl groups but the synthesis is difficult. On the top of that, due to the presence of the bulky substituent group, the compact structure of the pentalene backbone has not been effectively used.

Further, compounds having the pentalene backbone described in Patent Literature 1 and Non Patent Literatures 2 to 5 are also synthesized by utilizing the introduction of the sterically-bulky substituent group, stabilization by a benzo-condensed ring, or the like; yet the synthesis of compound having the pentalene backbone with various substituent groups has been difficult by a range in application of a substrate being narrow in the synthesis process, or the like. Further, it has not been reported that the compounds having the pentalene backbone described in Patent Literature 1 and Non Patent Literatures 2 to 5 are fluorescent molecules.

The present invention was made in view of the above circumstances and an object thereof is to provide a compound having a fluorescent chromophore, an ion concentration sensor comprising the compound, a reagent comprising the compound, a reagent kit provided with the reagent, and a precursor of the compound.

In addition, another object of the present invention is to provide a method for synthesizing the above compound.

Solution to Problem

The present inventor has intensively studied to find out for the first time that a triazapentalene backbone represented by the general formula 1 is a profoundly excellent fluorescent chromophore, and further has found out method of synthesizing the triazapentalene backbone comprising subjecting an organic azide having a leaving group and alkyne or a derivative thereof to a dipolar cycloaddition reaction.

The general formula 1

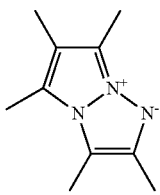

1

In order to achieve the above object, a compound according to a first point of view of the present invention has a triazapentalene backbone as a fluorescent chromophore.

The above-mentioned compound may have a structure represented by the general formula 2:

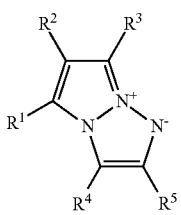

2

(wherein $R^1$, $R^2$, $R^3$, $R^4$ and $R^5$, same or different, represent substituent groups; and two or more groups of $R^1$, $R^2$, $R^3$, $R^4$ and $R^5$ may join together to form a ring).

At least one substituent group of the above-mentioned $R^1$, $R^2$, $R^3$, $R^4$, and $R^5$ may be an electron withdrawing group.

The above-mentioned substituent group of $R^2$ may be an electron donating group or electron withdrawing group; and the above-mentioned substituent group of $R^4$ and/or $R^5$ may be an electron withdrawing group.

The above-mentioned compound may have a constitute unit represented by the general formula 3:

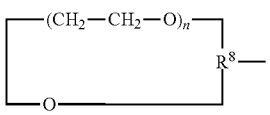

3

(wherein $R^8$ is an alkylene group with two carbon atoms or more which may be branched, or an arylene group that may comprise a substituent group with six carbon atoms or more).

An ion concentration sensor according to a second point of view of the present invention comprises the above compound.

A reagent according to a third point of view of the present invention comprises the above compound.

A reagent kit according to a fourth point of view of the present invention equips with at least one of the above reagents.

The maximum fluorescence wavelength of at least one of the above-mentioned reagent may be a maximum fluorescence wavelength selected from the group consisting of 400 nm or more and 430 nm and less, more than 430 nm and 480 nm or less, more than 480 nm and 530 nm or less, and more than 530 nm and 2000 nm or less.

A precursor of the above compound according to a fifth point of view of the present invention is represented by the general formula 4:

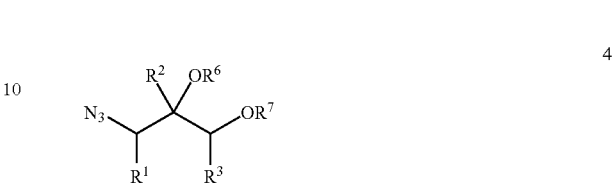

4

(wherein $R^1$, $R^2$ and $R^3$, same or different, represent substituent groups; and $R^6$ and $R^7$, same or different, represent substituent groups).

A method of synthesizing the above compound according to a sixth point of view of the present invention is characterized by comprising the step of subjecting an organic azide with a leaving group and an alkyne or a derivative thereof to a dipolar cycloaddition reaction in the presence of a catalyst promoting the dipolar cycloaddition reaction.

The method of synthesizing the above compound, which method synthesizing a compound comprising a structure represented by the general formula 2:

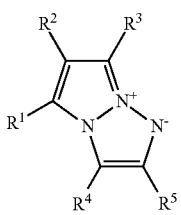

2 may comprise subjecting the above-mentioned organic azide presented by the general formula 4:

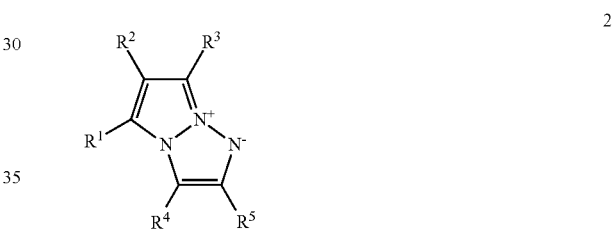

4 and the above-mentioned alkyne presented by the general formula 5:

5 or a derivative thereof to a dipolar cycloaddition reaction in the presence of a catalyst promoting the dipolar cycloaddition reaction.

(In the formulae, $R^1$, $R^2$, $R^3$, $R^4$ and $R^5$, same or different, represent substituent groups; and $R^6$ and $R^7$, same or different, represent substituent groups.)

Advantageous Effects of Invention

According to the present invention, it is possible to provide a compound having a fluorescent chromophore, an ion concentration sensor comprising the compound, a reagent comprising the compound, a reagent kit provided with the reagent, and a precursor of the compound.

According to the present invention, it is possible to provide a method of synthesizing the above compound.

DESCRIPTION OF EMBODIMENTS

Figure 1:
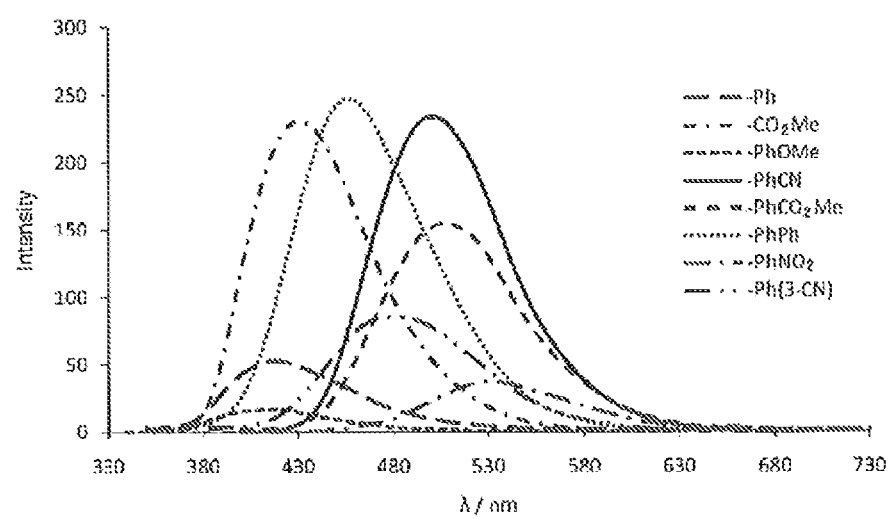
FIG. 1 is a graph chart showing the result of the example of the present invention.

In structural formulae herein, unless a steric structure or the like is in particular provided, a compound represented by the structural formula herein includes various stereoisomers such as a tautomer, geometric isomer, or optical isomer, and a mixture thereof.

The present invention relates to a compound having a triazapentalene backbone as a fluorescent chromophore. The triazapentalene backbone has a structure represented by the general formula 1, and the compound having a triazapentalene backbone is a compound in which the backbone is chemically bound with hydrogen atom, substituent groups or other molecules.

In relation to modes for carrying out the present invention, as an example of the compound having a triazapentalene backbone as a fluorescent chromophore and the method of synthesis thereof, a compound having a structure represented by the general formula 2 and a method of synthesis thereof will be described in detail below.

In a compound having a structure represented by the general formula 2 as a fluorescent chromophore and a method of synthesis thereof, substituent groups ($R^1$, $R^2$, $R^3$, $R^4$, and $R^5$) in the general formula 2, the general formula 4, and the general formula 5 are appropriately selected in a range that suits the object of the present invention. Representative examples of the substituent groups ($R^1$, $R^2$, $R^3$, $R^4$, and $R^5$) include, but not limited to, the following. In the formulae, $R^1$, $R^2$, $R^3$, $R^4$ and $R^5$ may be same or different, and two or more groups of $R^1$, $R^2$, $R^3$, $R^4$ and $R^5$ may join together to form a ring. However, it is preferred that the ring that is newly formed by bonding does not have aromaticity. Further, $R^6$ and $R^7$ may be same or different. Further, $R^1$, $R^2$, $R^3$, $R^4$ and/or $R^5$ may be a hydrogen atom without being substituted with a substituent group.

Examples of the substituent groups of $R^1$ to $R^5$ of triazapentalenes which are compounds having a structure represented by the general formula 2 include alkyl groups preferably having 1 to 12 carbon atoms such as a methyl group, ethyl group, propyl group, butyl group, pentyl group, or hexyl group, which may further have substituent groups; and cycloalkyl groups preferably having 1 to 18 carbon atoms such as a cyclopropyl group, cyclobutyl group, cyclopentyl group, or cyclohexyl group, which may further have substituent groups.

In addition, examples of the substituent groups of $R^1$ to $R^5$ of triazapentalenes which are compounds having a structure represented by the general formula 2 include aryl groups preferably having 6 to 30 carbon atoms, such as a phenyl group, methoxyphenyl group, methoxycarbonylphenyl group, methyl ether ketone phenyl group, biphenyl group, cyanophenyl group, nitrophenyl group, tolyl group, or xylyl group, which may further have substituent groups; carbonyl groups preferably having 1 to 12 carbon atoms, such as an aldehyde group, keto group such as a methyl keto group carboxy group, ester group, or amide group, which may further have substituent groups; alkyl groups preferably having 1 to 12 carbon atoms, such as chain-like alkyl groups such as a methyl group or butyl group, or benzyl group, which may further have substituent groups; silyl groups preferably having 3 to 12 carbon atoms, such as a trimethylsilyl group, triethylsilyl group, or triisopropylsilyl group, which may further have substituent groups; haloalkylsulfonate groups preferably having 1 to 12 carbon atoms such as a trifluoromethanesulfonate (Tf) group; aryl sulfonate groups preferably having 6 to 30 carbon atoms such as a toluenesulfonate (Ts) group, or benzenesulfonate group; alkyl sulfonate groups preferably having 1 to 12 carbon atoms such as a methane sulfonate (Ms) group; alkoxycarbonyl groups preferably having 1 to 12 carbon atoms such as acetoxy; and halogen atoms (fluorine atom, chlorine atom, bromine atom, and iodine atom).

Further, in particular, examples of the substituent group of $R^5$ include alkyl groups preferably having 1 to 12 carbon atoms such as an ethyl group, propyl group, butyl group, pentyl group, or hexyl group, which do not have substituent groups; alkyl groups preferably having 1 to 12 carbon atoms such as a methyl group, ethyl group, propyl group, butyl group, pentyl group, or hexyl group, which further have substituent groups; cycloalkyl groups preferably having 1 to 18 carbon atoms such as a cyclopropyl group, cyclobutyl group, cyclopentyl group, or cyclohexyl group, which may have substituent groups; aryl groups preferably having 6 to 30 carbon atoms such as a methoxyphenyl group, methoxycarbonylphenyl group, methyl ether ketone phenyl group, biphenyl group, cyanophenyl group, nitrophenyl group, tolyl group, or xylyl group, which do not have substituent groups; aryl groups preferably having 6 to 30 carbon atoms such as a phenyl group, methoxyphenyl group, methoxycarbonylphenyl group, methyl ether ketone phenyl group, biphenyl group, cyanophenyl group, nitrophenyl group, tolyl group, or xylyl group, which further have substituent groups; carbonyl groups preferably having 1 to 12 carbon atoms such as an aldehyde group, keto group such as methyl keto group, carboxy group, ester group, amide group; silyl groups preferably having 3 to 18 carbon atoms such as a trimethylsilyl group, triethylsilyl group, or triisopropylsilyl group; haloalkylsulfonate groups preferably having 1 to 12 carbon atoms such as a trifluoromethanesulfonate (Tf) group; aryl sulfonate groups preferably having 6 to 30 carbon atoms such as a toluenesulfonate (Ts) group or benzenesulfonate group; alkyl sulfonate groups preferably having 1 to 12 carbon atoms such as a methane sulfonate (Ms) group; alkoxycarbonyl groups preferably having 1 to 12 carbon atoms such as acetoxy; and halogen atoms (fluorine atom, chlorine atom, bromine atom, and iodine atom). Of these, it is preferred to be substituent groups having an electron-withdrawing property described later.

The substituent group that is directly or indirectly introduced on a triazapentalene backbone preferably has an electron-withdrawing property; and examples thereof include, but not limited to, a cyano group, carboxyl groups preferably having 1 to 12 carbon atoms; a nitro group; an acyl group; alkyloxycarbonyl groups preferably having 2 to 18 carbon atoms; aryl groups preferably having 6 to 30 carbon atoms such as cyanophenyl groups preferably having 6 to 30 carbon atoms such as a 2-cyanophenyl group, 3-cyanophenyl group, or 4-cyanophenyl group, which may have substitutions by halogen atoms, or alkoxycarbonyl phenyl groups preferably having 8 to 30 carbon atoms such as a methoxycarbonylphenyl group; aryloxycarbonyl groups preferably having 7 to 30 carbon atoms; alkylsulfonyl groups preferably having 1 to 12 carbon atoms; arylsulfonyl groups preferably having 6 to 30 carbon atoms; haloalkylsulfonate groups preferably having 1 to 12 carbon atoms; aryl sulfonate groups preferably having 6 to 30 carbon atoms; alkyl sulfonate groups preferably having 1 to 12 carbon atoms; ester groups preferably having 2 to 18 carbon atoms; amide groups preferably having 1 to 18 carbon atoms, perfluoroalkyl groups preferably having 1 to 12 carbon atoms, perfluoroalkylthio groups preferably having 1 to 12 carbon atoms, perfluoroalkylcarbonyl groups preferably having 2 to 18 carbon atoms, sulfonamide groups preferably having 2 to 18 carbon atoms, which may have substituent groups, acyloxy groups preferably having 2 to 18 carbon atoms, carbamoyl groups preferably having 1 to 12 carbon atoms, alkoxycarbonyl groups preferably having 2 to 18 carbon atoms, dialkylphosphono groups preferably having 2 to 18 carbon atoms, diarylphosphono groups preferably having 12 to 40 carbon atoms, diarylphosphinyl groups preferably having 12 to 40 carbon atoms, alkylsulfinyl groups preferably having 1 to 12 carbon atoms, aryl sulfinyl groups preferably having 6 to 30 carbon atoms, a sulfonyloxy group, acylthio groups preferably having 1 to 12 carbon atoms, a sulfamoyl group, thiocyanate groups preferably having 2 to 18 carbon atoms, thiocarbonyl groups preferably having 1 to 12 carbon atoms, alkoxycarbonyl groups preferably having 2 to 18 carbon atoms, and halogen atoms such as a fluorine atom, chlorine atom, bromine atom, or iodine atom. In accordance with the present description, a functional group having an electron-withdrawing property (electron withdrawing group) refers to a functional group or atom whose Hammett substituent constant $\sigma_p$ value is a positive value. By at least one of $R^1$, $R^2$, $R^3$, $R^4$, and $R^5$ being the functional group having the electron-withdrawing property, it is possible to increase the intensity of fluorescence of the compound having a structure represented by the general formula 2. Further, it is possible to the yield of synthesis of the compound having a structure represented by the general formula 2 described later.

Examples of the aryl groups preferably having 6 to 30 carbon atoms that has substitution with halogen atoms include a fluorophenyl group such as a pentafluorophenyl group, or trifluorophenyl group.

Further, examples of the alkylsulfonyl groups preferably having 1 to 12 carbon atoms include a mesyl group, ethylsulfonyl group, and propylsulfonyl group.

Further, examples of the arylsulfonyl groups preferably having 6 to 30 carbon atoms include a benzenesulfonyl group and toluenesulfonyl group.

Further, examples of the haloalkylsulfonate groups preferably having 1 to 12 carbon atoms include a trifluoromethanesulfonate (Tf) group.

Further, examples of the aryl sulfonate groups preferably having 6 to 30 carbon atoms include a toluenesulfonate (Ts) group and benzenesulfonate group.

Further, examples of the alkyl sulfonate groups preferably having 1 to 12 carbon atoms include a methane sulfonate (Ms) group.

Further, examples of the perfluoroalkyl groups preferably having 1 to 12 carbon atoms include a trifluoromethyl group and pentafluoroethyl group.

Further, examples of the perfluoroalkylthio groups preferably having 1 to 12 carbon atoms include a trifluoromethylthio group and pentafluoroethylthio group.

Further, examples of the perfluoroalkylcarbonyl groups preferably having 2 to 18 carbon atoms include a trifluoroacetyl group and pentafluoroethylcarbonyl group.

Further, examples of the ester groups preferably having 2 to 18 carbon atoms include a methyl ester group and ethyl ester group.

Further, examples of the sulfonamide groups preferably having 1 to 18 carbon atoms include a sulfonamide group, dimethylamino sulfonyl, diethylamino sulfonyl group, and diphenylamino sulfonyl.

Further, examples of the alkoxycarbonyl groups preferably having 2 to 18 carbon atoms include an acetoxy carbonyl group.

Further, more preferred are functional groups having an electron-withdrawing property whose Hammett substituent constant $\sigma_p$ value is 0.20 or more. Examples thereof include, but not limited to, an acyl group, acyloxy group, carbamoyl groups preferably having 1 to 12 carbon atoms, alkoxycarbonyl groups preferably having 2 to 18 carbon atoms, aryloxycarbonyl groups preferably having 7 to 30 carbon atoms, a cyano group, a nitro group, dialkylphosphono groups preferably having 2 to 18 carbon atoms, a diarlphosphono group, diarylphosphinyl groups preferably having 12 to 40 carbon atoms, alkylsulfonyl groups preferably having 1 to 12 carbon atoms, aryl sulfinyl groups preferably having 6 to 30 carbon atoms, alkylsulfonyl groups preferably having 1 to 12 carbon atoms, arylsulfonyl groups preferably having 6 to 30 carbon atoms, haloalkylsulfonate groups preferably having 1 to 12 carbon atoms, aryl sulfonate groups preferably having 6 to 30 carbon atoms, alkyl sulfonate groups preferably having 1 to 12 carbon atoms, a sulfonyloxy group, acylthio groups preferably having 1 to 12 carbon atoms, a sulfamoyl group, thiocyanate groups preferably having 2 to 18 carbon atoms, and thiocarbonyl groups preferably having 1 to 12 carbon atoms. By substituting with the functional group whose Hammett substituent constant $\sigma_p$ value is 0.20 or more as the functional group having the electron-withdrawing property, it is possible to further increase the intensity of fluorescence of the compound having a structure represented by the general formula 2. Further, it is possible to further increase the yield of synthesis of the compound having a structure represented by the general formula 2 described later.

Further, it is preferred that the substituent group of $R^4$ and/or $R^5$ which is a negative ring of the triazapentalene backbone be an electron withdrawing group, and besides, that $R^1$, $R^2$ and/or $R^3$ which is a positive ring of the triazapentalene backbone be substituted with an electron donating group or electron withdrawing group. It is more preferred that the substituent group of $R^4$ and/or $R^5$ be the above-mentioned electron withdrawing group, and besides, that $R^2$ be substituted with an electron donating group or electron withdrawing group. In this case, $R^1$ and/or $R^3$ may be substituted or may not be substituted. Further, it is still more preferred that the substituent group of $R^5$ be the above-mentioned electron withdrawing group, and besides, that the substituent group of $R^2$ be an electron donating group or electron withdrawing group. In this case, $R^1$, $R^3$ and/or $R^4$ may be substituted or may not be substituted. Further, it is also still more preferred that the substituent group of $R^5$ be the above-mentioned electron withdrawing group, and besides, that the substituent group of $R^2$ be an electron donating group. In the present description, a functional group having an electron donating property (electron donating group) refers to a functional group or atom whose Hammett substituent constant $\sigma_p$ value is a negative value.

By a state where the substituent group of $R^4$ and/or $R^5$ is an electron withdrawing group, and besides, substituent group of $R^2$ is an electron donating group, concurrently with fluorescence chromogenic color of the compound having a structure represented by the general formula 2 being regulated by effects of the electron withdrawing group of $R^4$ and/or $R^5$, it is possible to more increase the intensity of fluorescence of compound having a structure represented by the general formula 2 by Push-Pull effects between the electron donating group at $R^2$ and the electron withdrawing group at $R^4$ and/or $R^5$. That is, it is possible to more enhance the detection of fluorescence.

The above-mentioned electron donating group is appropriately selected in a range that exerts effects of the present embodiment. Examples thereof include, but not limited to, alkyl groups preferably having 1 to 12 carbon atoms such as a methyl group, ethyl group, propyl group, butyl group, pentyl group, or hexyl group; cycloalkyl groups preferably having 1 to 18 carbon atoms such as a cyclopropyl group, cyclobutyl group, cyclopentyl group, or cyclohexyl group; alkoxy groups preferably having 1 to 12 carbon atoms such as a methoxy group, ethoxy group, or butoxy group; aryl groups preferably having 6 to 30 carbon atoms such as a phenyl group, methoxyphenyl group, methoxycarbonylphenyl group, methyl ether ketone phenyl group, biphenyl group, tolyl group, or xylyl group; functional groups preferably having 1 to 30 carbon atoms containing a hetero atom such as oxygen, sulfur, or nitrogen, such as an amino group, acyloxy group that may further have substituent groups, carbamoyl group, sulfonyloxy group, acylthio group, or sulfamoyl group.

Further, by a state where the substituent group of $R^4$ and/or $R^5$ is an electron withdrawing group, and besides, substituent group of $R^2$ is an electron donating group, concurrently with fluorescence chromogenic color of the compound having a structure represented by the general formula 2 being regulated by effects of the electron withdrawing group of $R^4$ and/or $R^5$, it is possible to shift the fluorescence wavelength of the compound having a structure represented by the general formula 2 toward the short wavelength side by the electron withdrawing group of $R^2$, which makes it possible to regulate the fluorescence wavelength and fluorescent color by the electron withdrawing group of both $R^2$ and $R^5$.

The substituent groups ($R^6$ and $R^7$) of the compound having a structure represented by the general formula 4 is appropriately selected in a range that suits the object of effects of the present invention. Representative examples of the substituent groups ($R^6$ and $R^7$) include, but not limited to, haloalkylsulfonate groups preferably having 1 to 12 carbon atoms such as a trifluoromethanesulfonate (Tf) group, aryl sulfonate groups preferably having 6 to 30 carbon atoms such as a toluenesulfonate (Ts) group or benzenesulfonate group, alkyl sulfonate groups preferably having 1 to 12 carbon atoms such as a methane sulfonate (Ms) group, alkoxycarbonyl groups preferably having 2 to 18 carbon atoms such as acetoxy, and halogen atoms (fluorine atom, chlorine atom, bromine atom, and iodine atom). Further, $R^6$ and/or $R^7$ may be a hydrogen atom, without being substituted.

It is possible to synthesize the compound of the present invention represented by the general formula 2 by a method described in the following reaction formula (1).

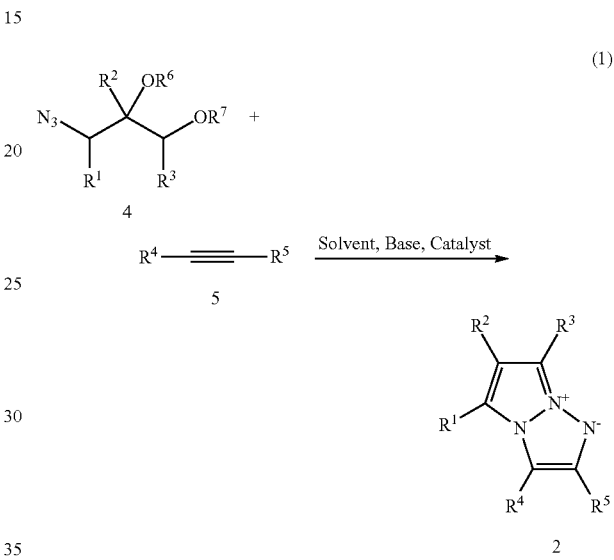

[In the formula, $R^1$, $R^2$, $R^3$, $R^4$, $R^5$, $R^6$, and $R^7$ represent the same meaning as in general formula 2, the general formula 4, and the general formula 5.]

In the reaction formula (1), it is possible to synthesize a compound having a structure represented by the general formula 2 by subjecting a compound having the structure represented by the general formula 4 (precursor) and alkyne represented by the general formula 5 or a derivative thereof to a dipolar cycloaddition reaction in a solvent, in the presence of a base, in the presence of a catalyst promoting the dipolar cycloaddition reaction, and in the absence or presence of a ligand. The dipolar cycloaddition reaction is a reaction forming a carbocyclic ring by addition of a molecule having intramolecularly both positive and negative charges (dipole) to an unsaturated bond.

A solvent used in the reaction represented by the reaction formula (1) is appropriately selected in a range that suits the object of the present invention. As long as the solvent does not in particular reacted with the general formula 2, the general formula 4 and the general formula 5, examples thereof include, but not limited to, ethers such as tetrahydrofuran (THF), diethyl ether, diisopropyl ether, 1,2-dimethoxyethane (DME), or dioxane; water, halogenated hydrocarbons such as dichloromethane or chloroform, aromatic hydrocarbons such as benzene, toluene or xylene, aliphatic hydrocarbons such as hexane or heptane, aprotic polar solvent such as dimethylacetamide (DMA), 1,3-dimethyl-2-imidazolidinone (DMI), or 1-methyl-2-pyrrolidone (NMP), nitriles such as acetonitrile or propionitrile, alcohols such as tert-butanol or isopropanol, and water.

A base used in the reaction represented by the reaction formula (1) is appropriately selected in a range that suits the object of the present invention. Examples thereof include, but not limited to, a basic nitrogen-containing organic compound. Examples of the above basic nitrogen-containing organic compound include alkylamines such as triethylamine, lutidine, pyridine, 4-(dimethylamino)pyridine (DMAP), and 1,8-diazabicyclo[5.4.0]-undecene-7-ene (DBU). In addition, it is possible to use an inorganic base that is weakly basic such as potassium carbonate, sodium hydrogen carbonate, and cesium carbonate. The amount of these bases used is particularly restricted limit; and when the above organic salt is used, it is possible to use the salt as a solvent.

A catalyst used in the reaction represented by the reaction formula (1) is appropriately selected in a range that suits the object of the present invention. Examples thereof include, but not limited to, copper catalyst, for example, copper by itself, copper iodide (I), copper chloride (I), copper oxide (I), copper bromide (I) tristriphenylphosphine complex, trifluoromethanesulfonic acid copper (I) benzene complex or the like; and a catalyst promoting a dipolar cycloaddition reaction such as a ruthenium catalyst. In cases where the ruthenium catalyst is used here, the $R^4$ and $R^5$ positions in the structure the general formula 2 are reversed, as compared with cases where the copper catalyst is used.

A ligand used on the reaction represented by the reaction formula (1) is appropriately selected in a range that suits the object of the present invention such that a catalyst is more homogeneous in a solution. As long as the ligand does not in particular reacted with the general formula 2, the general formula 4 and the general formula 5, examples thereof include, but not limited to, multidentate amines such as amino alcohol or diamine Examples of the multidentate amines include, but not limited to, bis[2-(dimethylamino)ethyl]ether, N,N'-tetramethylpentane-1,5-diamines, and 5-dimethylamino-1-pentanol.

A reaction temperature and reaction time of the above reaction is appropriately selected in a range that suits the object of the present invention. It is possible to carry out the reaction, for example, at −20° C. to 60° C., preferably at 10° C. to 40° C. and more preferably at 15° C. to 25° C. Further, it is possible to set a reaction time of, for example, 0.5 hours to 10 hours, preferably 0.5 hours to 5 hours, and more preferably 1 hour to 3 hours.

A reaction atmosphere of the above reaction is appropriately selected in a range that suits the object of the present invention. For example, it is possible to use noble gases such as helium, or argon or inert gases such as nitrogen gas. Further, the reaction may be carried out in air.

It is possible to synthesize the compound having structural formula represented by the general formula 4 (precursor) in the reaction formula (1), for example, in the following manner Halogenated alcohol such as commercially available chloropropanediol is first subjected, with a azide compound such as commercially available sodium azide, 4-dodecylbenzenesulfonyl azide, 4-acetylaminobenzenesulfonyl azide, diphenylphosphoryl azide, trimethylsilyl azide, to an $S_N2$ substitution reaction at a temperature of, for example, 50° C. or more and 150° C. or less, thereby obtaining a compound (azide-modified alcohol) (azidation). Next, the generated azide-modified alcohol is subjected to, with organic sulfonic acid such as commercially available trifluoromethanesulfonic anhydride, a triflation reaction using, for example, a dry ice (registered trademark)-acetone cooling medium or the like at a temperature of −100° C. or more and −10° C. or less, which thereby enables a compound having the structural formula represented by the general formula 4 to be synthesized.

It is possible to synthesize alkyne represented by the general formula 5 or a derivative thereof in the reaction formula (1) other than commercially available ones by partial oxidation of alkene or a derivative thereof, or the like. The alkyne or a derivative thereof is appropriately selected in a range that exerts effects of the present invention; and may be internal alkyne or a derivative thereof or may be terminal alkyne or a derivative thereof. Examples thereof include, but not limited to, acetylene, propyne, phenyl acetylene, diphenyl acetylene, methyl propiolate, nitrophenyl acetylene, methoxy phenyl acetylene, cyanophenylacetylene, and methoxycarbonyl phenyl acetylene.

A compound having a triazapentalene backbone is an aromatic compound with a $10\pi$ electron system by effects of the unshared electron pair on nitrogen, and therefore is a stable compound. In addition, the compound is a fluorescent molecule that emits strong fluorescence in spite of a compact structure thereof, has water-solubility. It is possible to readily introduce a functional group having fluorescence into the compound. Further, the compound is a new fluorescent molecule comprising many characteristics in combination, which characteristics include capability of regulating the fluorescence wavelength also by changing a solvent as well and feasibility of simple and efficient synthesis thereof. Thus, it is possible to provide a wavelength regulation-type fluorescent molecule by a compound having a triazapentalene backbone capable of emitting light in various wavelength regions in one fluorescent chromophore.

That is, the compound having fluorescent chromophore according to the present invention is, as compared with conventional fluorescent molecules, very compact in basic structure as a fluorescent chromophore and concurrently has high quantum yield and it is therefore possible to greatly improve the limit of detection of fluorescence.

Further, because the compound having fluorescent chromophore according to the present invention has a triazapentalene backbone, difference between absorption wavelength and fluorescence wavelength (Stokes shift) is large. Thus, when the compound having fluorescent chromophore according to the present invention is irradiated, difference between the wavelength of irradiating light (background light) and detected fluorescence wavelength is large and thus the color of the background light and detected fluorescent color is less likely to overlap, which makes it possible to more clearly capture the fluorescent color. In particular, use of the fluorescent chromophore according to the present invention makes it possible to obtain Stokes shift that is, for example, 100 nm or more even in a fluorescence wavelength, for example, above 500 nm. In addition, the use makes it possible to obtain clear fluorescence even in cases where a substituent group having a tendency to absorb light such as a nitro group is contained.

Further, the compound having fluorescent chromophore according to the present invention has a triazolium ion structure having intramolecularly zwitter ion and therefore has an amphipathic property exhibiting solubility in both an organic solvent and water. Thus, it is possible to use the compound in an aqueous solution. Therefore, when the compound is used in a study on biologically relevant functions, observation of fluorescence is feasible in a more natural way.

Further, it is possible to readily introduce the compound having fluorescent chromophore according to the present invention in one step by a fluorescence click reaction in various solvents including water. That is, the triazole ring generated by the fluorescence click reaction by itself is a fluorescence group, and it is therefore possible to introduce a fluorescent labeling group concurrently with linking with other labeling groups and functional molecules.

In the compound having fluorescent chromophore according to the present embodiment, it is possible to readily change fluorescence wavelength in accordance with difference on the electronic state of substituent groups $R^1$ to $R^5$. The fluorescent molecule according to the present embodiment has large dipole moment in a compact structure thereof and this is directly coupling with substituent groups ($R^1$, $R^2$, $R^3$, $R^4$, and $R^5$), which readily enables a change in the transition moment due to changes in the electronic state of the substituent groups ($R^1$, $R^2$, $R^3$, $R^4$, and $R^5$). That is, the change of the substituent groups ($R^1$, $R^2$, $R^3$, $R^4$, and $R^5$) makes it possible to readily change the fluorescence wavelength. In addition, change of polarity of solvent by changing the type of the solvent makes it possible to readily change the fluorescence wavelength of the above compound.

In the compound having fluorescent chromophore according to the present embodiment, it is possible to predict fluorescence wavelength by the Hammett constant of substituent group. Thus, it is possible to design the fluorescence wavelength of a compound having a fluorescent chromophore to regulate the fluorescent color only by changing the substituent group without changing the fluorescent chromophore (triazapentalene backbone) to use the same fluorescent chromophore. Hence, without changing the intrinsic physical property, biological activity or the like of the compound having the fluorescent chromophore (that is, without practically changing behavior of the compound having the fluorescent chromophore in each fluorescent color), molecular design tailored to the fluorescent color is readily feasible. On the other hand, because, the fluorescent color has been conventionally regulated by changing the fluorescent chromophore itself, the molecular design tailored to the fluorescent color has been very difficult and, in addition, there have been some cases where the intrinsic physical property, biological activity or the like of the compound changes.

In accordance with the present embodiment, a reaction with an azide compound (precursor) that is readily derived in two steps from, for example, a commercially available inexpensive compound such as 3-chloro-1,2-propanediol enables fluorescent molecules having the triazapentalene backbone with various substituent groups to be readily synthesized in high yield. Thus, introduction into various compounds is easy; and it is possible to utilize the compound having the fluorescent chromophore according to the present invention in a number of fields.

The fluorescent molecule of the compound according to the present invention has intramolecularly a zwitter ion and thus is easy to be affected by changes in external milieu, which enables exhibition of significant solvatochromic fluorescence. Thus, changes of luminescent color are observed by difference in the polarity of the surroundings; and it is therefore possible to know the localization of the compound having fluorescent chromophore inside cells or the like by changes of the luminescent color. Many of the conventional solvatochromic fluorescence molecules are, as described above, large in molecular size and are, in some cases, difficult to be taken up into cells. Yet, the fluorescent molecule according to the present embodiment has a smaller structure and is therefore easily taken up into cells. Hence, it is possible to use the fluorescent molecule according to the present embodiment as a reagent. The application of the reagent is appropriately selected in a range that exerts effects of the present invention. Examples thereof include, but not limited to, biochemical reagents employed in chemical biology, medical diagnosis, bacteria detection or the like.

Further, it is possible to combine the reagents according to the present embodiment to use as a reagent kit. That is, in accordance with the present embodiment, because it is possible to regulate the fluorescence wavelength by changing the substituent group, plural reagents developing various fluorescent colors are produced by changing the substituent group. It is possible to combine the plural reagents according to the present embodiment, dissolving solution in which the plural reagents are dissolved, solvent, other reagents and the like to use the reagent kit. The maximum fluorescence wavelength of the reagent used in the reagent kit is appropriately selected in a range that exerts effects of the present invention. The maximum fluorescence wavelength is selected from the group consisting of, without limitation, for example, a maximum fluorescence wavelength of not less than 400 nm and not more than 430 nm (blue fluorescent color), a maximum fluorescence wavelength of more than 430 nm and not more than 480 nm (green fluorescent color), a maximum fluorescence wavelength of more than 480 nm and not more than 530 nm (yellow fluorescent color), and a maximum fluorescence wavelength of more than 530 nm and not more than 2000 nm (red fluorescence wavelength). The reagent kit according to the present embodiment may be required to comprise the reagent having the maximum fluorescence wavelength in at least one of those ranges. That is, the reagent kit according to the present embodiment may contain only one of the reagents according to the present embodiment having the above four ranges of fluorescence wavelength, may contain two of the reagents according to the present embodiment having the above four ranges of fluorescence wavelength, may contain three and may contain four. For example, the reagent kit according to the present embodiment may include only the reagent according to the present embodiment having a fluorescence wavelength of 415 nm; or may includes the reagent according to the present embodiment having a fluorescence wavelength of 420 nm, the reagent according to the present embodiment having a fluorescence wavelength of 450 nm, the reagent according to the present embodiment having a fluorescence wavelength of 500 nm, and the reagent according to the present embodiment having a fluorescence wavelength of 550 nm.

It is noted that the present invention is not limited to the above modes for carrying out the invention and various variations and applications are allowed.

For example, although a mode where the triazapentalene backbone represented by the general formula 1 has substitutions with the substituent groups of $R^1$ to $R^5$ represented by the general formula 2 has been described in the present embodiment, a substance other than the substituent group may bind to the triazapentalene backbone represented by the general formula 1 in a range that exerts effects of the present invention. Examples of what may bind to the triazapentalene backbone include, but not limited to, metal chelating agent such as mugineic acids; biologically active substance such as siderophore, nucleic acid, amino acid, terpene, alkaloid, polyether, or poly phenol; functional molecule such as calixarene, rotaxane, porphyrin, or dendrimer; and molecule such as a phospholipid, carbohydrate chain, peptide, DNA, RNA, enzyme, protein, or high molecular weight molecule such as a natural or synthetic polymer. Further, an aromatic ring such as a benzene ring may condense to the triazapentalene backbone represented by the general formula 1.

Further, although a mode where the substituent groups of $R^1$ to $R^5$ are substituted in the synthesis stage of the compound having the structure represented by the general formula 2 has been described in the present embodiment, the substituent groups of $R^1$ to $R^5$ may be substituted after the above compound is synthesized. Further, substances such as biologically active substances or molecules such as a functional molecule or high molecular weight molecule, which are mentioned previously, may be bound in the synthesis stage of the compound having the triazapentalene backbone represented by the general formula 1, or may be bound after the compound having the triazapentalene backbone is synthesized.

Further, although a mode where the compound is synthesized by subjecting a compound having the structure represented by the general formula 4 and alkyne represented by the general formula 5 or a derivative thereof to a dipolar cycloaddition reaction in a solvent, in the presence of a base, and in the presence of the catalyst promoting a dipolar cycloaddition reaction has been described in the present embodiment, the compound having the triazapentalene backbone represented by the general formula 1 needs only be synthesized by subjecting an organic azide having a leaving group and an azide functional group and alkyne or a derivative thereof to a dipolar cycloaddition reaction in the presence of a catalyst promoting the dipolar cycloaddition reaction. The organic azide compound having the leaving group is appropriately selected in a range that exerts effects of the present invention. Examples thereof include, but not limited to, organic azide compounds containing, for example, haloalkylsulfonate group such as a trifluoromethanesulfonate (Tf) group, aryl sulfonate group such as a toluenesulfonate (Ts) group, benzenesulfonate group, alkyl sulfonate group such as a methane sulfonate (Ms) group; and, for example, metal chelating agent such as mugineic acids; biologically active substance such as siderophore, nucleic acid, amino acid, terpene, alkaloid, polyether, or poly phenol; functional molecule such as calixarene, rotaxane, porphyrin, or dendrimer; and molecule such as a phospholipid, carbohydrate chain, peptide, DNA, RNA, enzyme, protein, or high molecular weight molecule such as a natural or synthetic polymer.

In the present description, a "leaving group" refers to an atom or substituent group that is released in a reaction of an organic azide and alkyne or a derivative thereof; and is appropriately selected in a range that exerts effects of the present invention. Examples thereof include, but not limited to, haloalkylsulfonate group such as a trifluoromethanesulfonate (Tf) group; aryl sulfonate group such as a toluenesulfonate (Ts) group or benzenesulfonate group; alkyl sulfonate group such as a methane sulfonate (Ms) group; alkoxycarbonyl group such as acetoxy; and halogen atom (fluorine atom, chlorine atom, bromine atom, iodine atom).

Further, $R^4$ or $R^5$ of the compound having a structure represented by the general formula 2 may be a substituent group having a cyclic constituent unit represented by the general formula 3. The compound in which the substituent group of $R^4$ or $R^5$ has cyclic constituent unit represented by the general formula 3 will be described below. In the general formula 3, n represents an integer; and $R^8$ represents an alkylene group having two carbon atoms or more that may be branched or an arylene group having six carbon atoms or more that may have substituent groups.

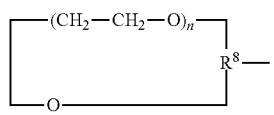

3

$R^4$ or $R^5$ having a cyclic constituent unit represented by the general formula 3 is appropriately selected in a range that suits the object of the present invention. Examples thereof include, but not limited to, crown ethers such as benzocrown ethers and alkyl crown ethers.

Examples of the benzocrown ethers include benzo-18-crown 6-ether, benzo-15-crown 5-ether, and benzo-12-crown 4-ether.

Examples of the alkyl crown ethers include methyl crown ethers such as methyl-18-crown 6-ether, methyl-15-crown 5-ether, or methyl-12-crown 4-ether; and ethyl crown ethers such as ethyl-18-crown 6-ether, ethyl-15-crown 5-ether, or ethyl-12-crown 4-ether.

It is possible to synthesize a compound in which the functional group of $R^4$ or $R^5$ of the compound having the structure represented by the general formula 2 has the cyclic constituent unit represented by the general formula 3 by, for example, the following reaction formula (2).

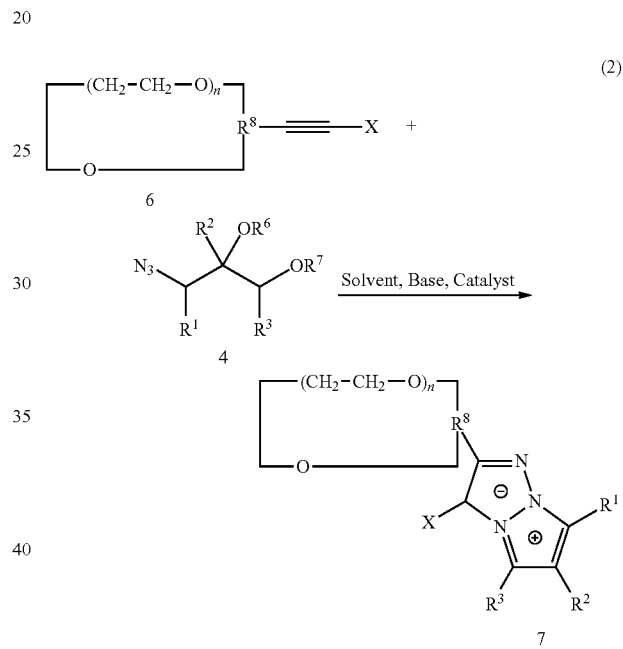

[wherein, $R^1$, $R^2$, $R^3$, $R^4$, $R^5$, $R^6$, and $R^7$ represent the same meaning as in the general formula 2. The substituent group $R^8$ represents an alkylene group having two carbon atoms or more that may be branched or an arylene group having six carbon atoms or more that may have substituent groups. X represents a substituent group.]

For example, as shown in the reaction formula (2), by reacting a crown ether compound having intramolecularly an ethynyl group, substituent group X, and substituent group $R^8$ represented by the general formula 6 with a compound (precursor) having a structure represented by the general formula 4 in a solvent in the presence of a base in the presence of a catalyst, a compound having a fluorescent molecule with a triazapentalene backbone as a fluorescent chromophore represented by the general formula 7 is synthesized. The substituent group X is appropriately selected in a range that suits the object of the present invention. Examples thereof include, but not limited to, a hydrogen atom, methyl group, phenyl group, and trimethylsilyl group.

A solvent, base, catalyst, reaction temperature and reaction time, which are used in a reaction represented by the reaction formula (2), are appropriately selected in a range that suits the object of the present invention; and it is for example possible to be same as in the reaction formula (1).

It is possible to synthesize a compound having the structure represented by the general formula 4 of the reaction formula (2) in the same manner as the compound having the structure represented by the general formula 4 of the reaction formula (1).

A compound having intramolecularly the structure represented by the general formula 2 in which the substituent group of $R^4$ or $R^5$ contains cyclic constituent unit represented by the general formula 3 exhibits increased fluorescence intensity by addition of a metal ion. Thus, it is possible to use the compound having intramolecularly a structure represented by the general formula 2 in which the substituent group of $R^4$ or $R^5$ contains cyclic constituent unit represented by the general formula 3 as an ion concentration sensor.

A compound having intramolecularly the structure represented by the general formula 2 in which the substituent group of $R^4$ or $R^5$ contains cyclic constituent unit represented by the general formula 3 according to the present embodiment has intramolecularly a zwitter ion; and it is therefore possible for the compound to have high functionality as an ion concentration sensor in, for example, an aqueous solution.

Similarly, a compound having a triazapentalene backbone represented by the general formula 1 may be bound with substance such as biologically active substances or molecule such as a functional molecule or high molecular weight molecule, including a cyclic constituent unit represented by the general formula 3. Similarly, compound having intramolecularly a structure represented by the general formula 1 including a cyclic constituent unit represented by the general formula 3 exhibits increased fluorescence intensity by addition of metal ions. Thus, it is possible to use the compound having a triazapentalene backbone represented by the general formula 1 and including cyclic constituent unit represented by the general formula 3 as an ion concentration sensor. Further, similarly, the compound having a triazapentalene backbone represented by the general formula 1 and including cyclic constituent unit represented by the general formula 3 has intramolecularly a zwitter ion; and it is therefore possible for the compound to have high functionality as an ion concentration sensor in, for example, an aqueous solution.

Further, a compound having the triazapentalene backbone represented by the general formula 1, or a compound having intramolecularly a structure represented by the general formula 2, which do not contain the cyclic constituent unit represented by the general formula 3, may be used as an ion concentration sensor. Also in this mode, the above class of compounds has intramolecularly a zwitter ion, which enables thereby the compounds to have high functionality as an ion concentration sensor in, for example, an aqueous solution.

Further, at least one of the substituent groups of the compound having fluorescent chromophore according to the present embodiment is a substituent group capable of condensation•substitution•addition•cross coupling with a compound having a nucleophilic or electrophilic substituent group. The substituent group capable of condensation•substitution•addition•cross coupling is appropriately selected in a range that exerts effects of the present invention. Examples thereof include, but not limited to, substituent groups such as an amino group, acylamino group, sulfo group, carboxyl group, hydroxyl group, thio group, ester group, amide group, thioamide group, carbonyl group, aldehyde group, trifluoromethanesulfonate group, carboxylic anhydride, acid chloride, chlorine, bromine, iodine, boric acid ester group, boric-acid group, or the like. The compound having fluorescent chromophore according to the present embodiment can also exhibit fluorescence in an aqueous solution in cases where the compound has substitutions with the above substituent group.

EXAMPLES

By way of examples, the present invention will be concretely described below.

Example 1

Synthesis of Azide Ditriflate

Commercially available 3-chloro-1,2-propanediol that is represented by the chemical formula 8 (1.9 g, 17.3 mmol) was dissolved in 17 mL of water. Sodium azide represented by the chemical formula 9 (1.4 g, 20.8 mmol) was added thereto and heated to reflux at 100° C. for 8 hours. Subsequently, the reaction solution was cooled to 0° C. and then the reaction mixture was added with a salt and extracted 5 times using ethyl acetate 30 mL. The collected organic layer was dried with anhydrous magnesium sulfate, filtered, and concentrated under reduced pressure, thereby obtaining 2.0 g of crude product of azide diol represented by the chemical formula 10 (reaction formula (3)).

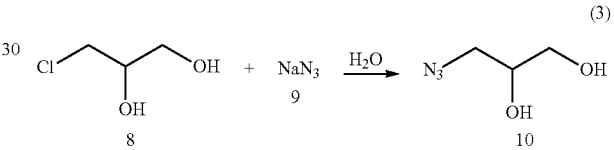

(3)

The crude product of azide diol represented by the chemical formula 10 was dissolved in 87 mL of dichloromethane and this solution was cooled in an acetone/dry ice (registered trademark) bath. This reaction solution was added with 2,6-lutidine (10.1 mL, 86.5 mmol) and then gently added with trifluoromethanesulfonic anhydride ($Tf_2O$) represented by the chemical formula 11 (5.8 mL, 34.6 mmol). The reaction solution was stirred for 10 minutes while cooled in an acetone/dry ice (registered trademark) bath, and gently added with saturated ammonium chloride solution 50 mL. The temperature of the resulting mixture solution was increased to room temperature (about 20° C.). This mixture solution was subjected to extraction 3 times using 50 mL of hexane. The collected organic layer was washed with saturated sodium chloride solution 80 mL, dried by adding anhydrous magnesium sulfate, filtered, and concentrated under reduced pressure, thereby obtaining a crude product of azide ditriflate represented by the chemical formula 12. The crude product of azide ditriflate was purified by silica gel column chromatography (developing solvent: hexane/ethyl acetate=95/1, 90/1 to 7/3), thereby obtaining, as a pale yellow oily product, azide ditriflate which is a precursor at the time of synthesizing a triazapentalene compound (5.38 g, yield 82%) (reaction formula (4)).

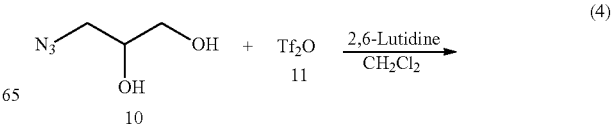

(4)

-continued

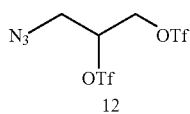

12

Example 2

Synthesis of Triazapentalene Compound (with the Substituent Group being $CO_2CH_3$)

Azide ditriflate represented by the chemical formula 12 (390 mg, 10 mmol) was dissolved in 102 mL of tetrahydrofuran, added with methyl propiolate represented by the chemical formula 13 (136 mL, 1.53 mmol), triethylamine (717 mL, 5.1 mmol), copper iodide (9.7 mg, 0.05 mmol), and stirred under argon atmosphere at room temperature (about 20° C.) for 2 hours. Subsequently, the reaction mixture solution was directly concentrated under reduced pressure using a rotatory evaporator, thereby obtaining a crude product methyl ester triazapentalene represented by the chemical formula 14. The crude product of triazapentalenes represented by the chemical formula 14 was purified by silica gel column chromatography (developing solvent:hexane/ethyl acetate=87/13, 62/38 to 60/40), thereby obtaining methyl ester triazapentalene represented by the chemical formula 14 (152 mg, yield 90%) as a pale yellow solid (reaction formula (5)). All of the substituent groups shown in Table 1 were bound to the $R^5$ position of a compound having a triazapentalene backbone. Further, unless otherwise noted, a compound having a triazapentalene backbone having a functional group shown in Table 1 was synthesized under the same conditions as described in Example 1 to Example 2 with a yield shown in Table 1. That is, under the same condition as in Example 1 and Example 2 except that the substituent group of $CO_2CH_3$ part in the chemical formula 13 of the reaction formula (5) was replaced with each of the substituent groups shown in Table 1 ($C_4H_9$, OMe, TMS, $CO_2Me$, phenyl group, biphenyl group, methoxyphenyl group, 3-cyanophenyl group, nitrophenyl group, methoxyperfluorophenyl group, trifluoromethanesulfonic acid ester phenyl group, methyl ester phenyl group, O-TBS, 1-cyanophenyl group, 2-cyanophenyl group, chlorophenyl group), a respective compound having a triazapentalene backbone with the functional group shown in Table 1 being bound to the $R^5$ position was obtained. In Table 1, (b) indicates that the concentration of acetylene in the reaction solvent was set to 0.1 mol/L; and (c) indicated that water was used as the solvent. Further, in Table 1, TMS represents a trimethylsilyl group and TBS represents a tert-butyldimethylsilyl group.

TABLE 1

—$C_4H_{10}$
84%

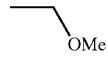
80%

—TMS
99%
—$CO_2Me$
(b) 90%

TABLE 1-continued

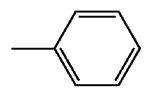

89%
(c) 56 %

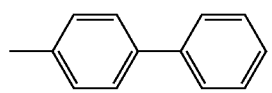

81%

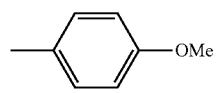

56%

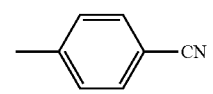

(b) 77%

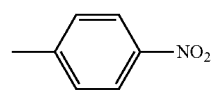

(b) 96%

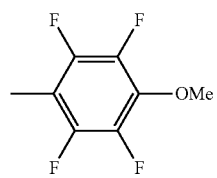

Yield data not available

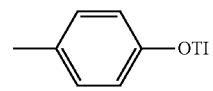

(b) 88%

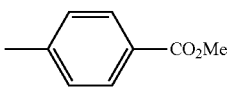

73%

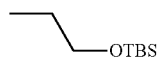

56%

TABLE 1-continued

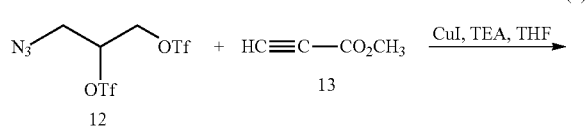

Example 3

Fluorescence Spectrum Measurement of Triazapentalenes

The fluorescence spectrum of various triazapentalenes that have been synthesized by the same method as described in Example 1 and Example 2 was measured. A method for measurement will be specifically described below.

As triazapentalenes, compounds with the substituent group being a phenyl group, methoxyphenyl group, 2-cyanophenyl group, methoxycarbonylphenyl group, methyl ester group, diphenyl group, 3-cyanophenyl group, and nitrophenyl group were used.

Each of the above compounds was made into solution with concentration shown in Table 2 using dichloromethane as a solvent. Using a fluorescence spectrophotometer (manufactured by Hitachi High-Technologies Corporation, F-4500), the ultraviolet absorption spectrum of each was measured and, as shown in Table 2, the absorption maximum wavelength ($\lambda_{max}$) was determined to be 326 nm to 412 nm. The concentration of a sample solution was adjusted such that the intensity (Abs.) of absorption maximum wavelength was 0.100±0.005, and using a spectrophotometer (manufactured by Hitachi High-Technologies Corporation, U-3500), each fluorescence spectrum was measured with excitation wavelength ($\lambda_{ex}$)=326 nm to 412 nm that was equal to absorption maximum wavelength. The fluorescence quantum yield was determined using 9,10-bis(phenyl ethynyl)anthracene (absolute fluorescence quantum yield=0.96) as a standard substance.

As a result of the measurement, as shown in FIG. 1 and Table 2, it was found that particularly strong relative quantum yield was obtained in a substrate with an electron withdrawing group being introduced. In FIG. 1 and Table 2, with regard to a substituent group, Ph represents a phenyl group, Me represents a methyl group, $CO_2Me$ represents a methyl ester group, OMe represents a methylalkoxy group, and CN represents a cyano group. Further, in Table $\lambda_{ex}$ represents excitation wavelength, $\epsilon$ represents a molar extinction coefficient, $\lambda_{em}$ represents emission wavelength, $\phi_r$ represents a relative fluorescence quantum yield using 9,10-bis(phenyl ethynyl)anthracene (absolute fluorescence quantum yield=0.96) as a standard, and "–" represents no measurement data available.

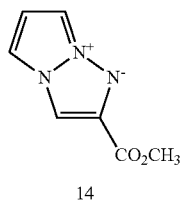

TABLE 2

| Triazapentalene compound | | | | |
|---|---|---|---|---|
| Substituent group | —Ph | —PhOMe | —PhCN | —PhCO$_2$Me |
| Measured concentration (mol/L) | 9.01 × 10$^{-5}$ | 5.67 × 10$^{-5}$ | 5.81 × 10$^{-5}$ | 4.68 × 10$^{-5}$ |
| $\lambda_{ex}$ (nm) | 326 | 330 | 381 | 376 |
| $\epsilon(10^3$ cm – M$^{-1}$) | 3.82 | 5.70 | 2.85 | 3.02 |

TABLE 2-continued

| $\lambda_{em}$ (nm) | 419 | 413 | 509 | 510 |
|---|---|---|---|---|
| $\phi_r$(%) | 3.0 | 6.2 | 18 | 51 |

| Triazapentalene compound | 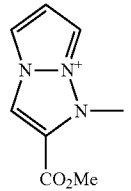 | 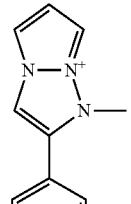Ph | 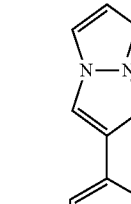NC | 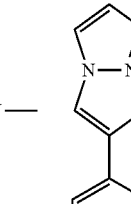$NO_2$ |
|---|---|---|---|---|
| Substituent group | —$CO_2Me$ | —Ph—Ph | —Ph(3-CN) | —$PhNO_2$ |
| Measured concentration (mol/L) | 7.93 × 10$^{-5}$ | 3.97 × 10$^{-5}$ | — | — |
| $\lambda_{ex}$ (nm) | 342 | 345 | 330 | 412 |
| $\epsilon(10^3$ cm – $M^{-1})$ | 2.63 | 4.79 | — | — |
| $\lambda_{em}$ (nm) | 431 | 456 | 481 | 556 |
| $\phi_r$(%) | 21 | 24 | — | 16 |

As shown in Table 2, strong relative fluorescence quantum yield ($\phi_r$=21%) was exhibited even in very small triazapentalenes with a methyl ester group alone being introduced. A more preferred range of relative fluorescence quantum yield is 10% or more, which facilitates observation with the unaided eye. In addition, it has been found that the relative fluorescence quantum yield further improves when an acid is added in the solution. Further, as shown in FIG. 1, it was found that stronger fluorescence intensity were obtained in triazapentalenes having substitution by a methyl ester group, diphenyl group, or cyan phenyl group.

Further, as shown in Table 2, unlike the fluorescence wavelength of conventional fluorescence agents, the fluorescence wavelength significantly changed in accordance with a pattern of the substituent groups ($R^1$ to $R^5$). In particular, as shown in Table 3 and FIG. 4 of Example 6 described later, as the electron-withdrawing property of substituent group ($R^1$ to $R^5$) increases, the fluorescence wavelength tended to shift to the long wavelength side. Thus, design of fluorescence wavelength that has been difficult to be in conventional fluorescent molecules is feasible in the compound having a triazapentalene backbone as the fluorescent chromophore according to the present example. It was found that making a data base of patterns of the functional group for substitution and fluorescence wavelength enabled various fluorescent molecules having the desired fluorescence wavelength to be produced, and enabled the fluorescent molecule of the present example to be widely used in a number of industries. Further, it was found that the introduction of the electron withdrawing group readily made the wavelength shift longer to a near-infrared region to thereby provide fluorescent molecules capable of reducing damages to living cells and capable of more inhibiting quenching by biological molecules, which made it possible to use the fluorescent molecules in a bioimaging industry such as a medical diagnosis device.

Example 4

Solvatochromic Fluorescence of Triazapentalenes

The fluorescence of a triazapentalene compound whose substituent group was -PhCN was measured in various solvents. A method for measurement will be specifically described below.

As solvents, dichloromethane (manufactured by Junsei Chemical Co., Ltd.), acetonitrile (manufactured by Kanto Chemical Co., Inc.), benzene (manufactured by Nacalai Tesque, Inc.), and acetone (manufactured by Nacalai Tesque, Inc.) were individually used.

Each of the triazapentalene compound whose substituent group was -PhCN was dissolved in the above solvent. With regard to the concentration of each solution, the concentration of solution with dichloromethane being used as the solvent was 5.81×10$^{-6}$ mol/L, the concentration of solution with acetonitrile being used as the solvent was 3.65×10$^{-6}$ mol/L, the concentration of solution with benzene being used as the solvent was 5.43×10$^{-6}$ mol/L, and the concentration of solution with acetone being used as the solvent was 6.63×10$^{-6}$ mol/L. Using a fluorescence spectrophotometer (manufactured by Hitachi High-Technologies Corporation, F-4500), the ultraviolet absorption spectrum was measured, and the absorption maximum wavelength ($\lambda_{max}$) was determined to be 382 nm. The concentration of a sample solution was adjusted such that the intensity (Abs.) of absorption maximum wavelength was 0.100±0.005, and using a spectrophotometer (manufactured by Hitachi High-Technologies Corporation, U-3500), the fluorescence spectrum was measured with excitation wavelength ($\lambda_{ex}$)=382 nm that was equal to absorption maximum wavelength. The fluorescence quantum yield was determined using 9,10-bis(phenyl ethynyl)anthracene (absolute fluorescence quantum yield=0.96) as a standard substance.

Figure 2:
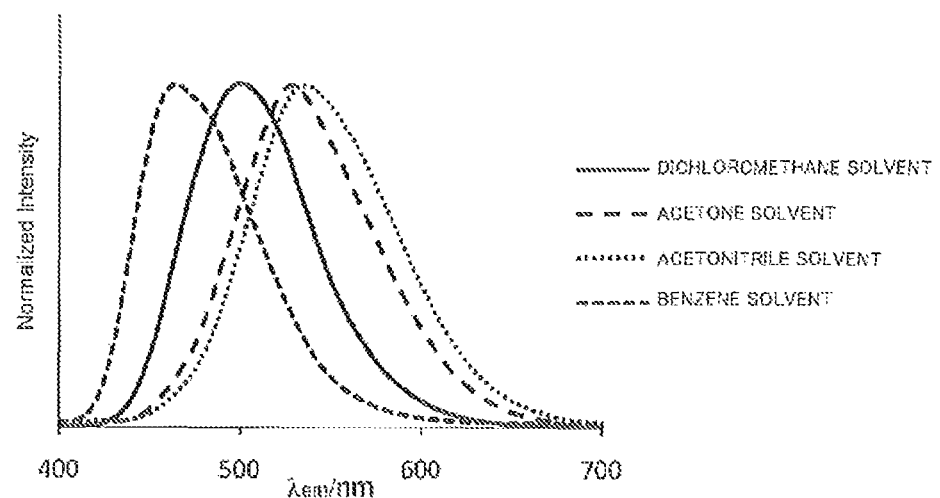
FIG. 2 is a graph chart showing the result of the example of the present invention.

When the fluorescence spectrum was measured, significant solvatochromism was observed (FIG. 2). Note that the vertical axis in FIG. 2 shows normalized intensity (Normalized Intensity).

As shown in FIG. 2, in association with the change in the polarity of solvent, the fluorescence wavelength is greatly changed and the luminescent color when visually observed was changed as well. With regard to the solvent polarity parameter $E_T$(kcal/mol, 25° C.) of each of the solvents shown in FIG. 2, dichloromethane exhibited $E_T$=41.1, acetone exhibited $E_T$=42.3, acetonitrile exhibited $E_T$=46.0, and benzene exhibited $E_T$=34.5. This measurement revealed that the fluorescence agent according to the present example greatly changed fluorescent color according to the surrounding environment in spite of having a compact structure; and the fluorescence agent was found to be feasible to be used as reagents for chemical biology that change fluorescent color thereof in accordance with intracellular localization of fluorescence agent.

Example 5

Ion Concentration Sensor Using Triazapentalenes

Acetylene-containing crown ether (4'-ethynyl benzo-18-crown 6-ether) represented by the chemical formula 15 that had been derived from commercially available crown ether in two steps was applied to the method of synthesizing triazapentalenes described in Examples 1 to 2, to synthesize crown ether containing intramolecularly triazapentalenes represented by the chemical formula 16 (reaction formula (6)).

(6)

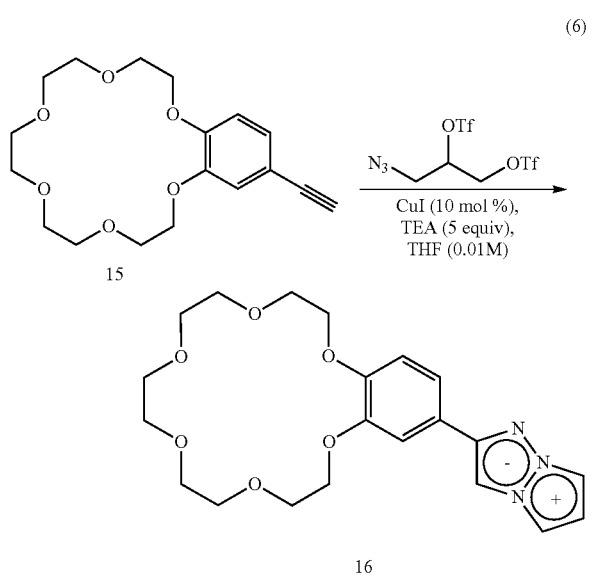

The acetylene-containing crown ether represented by the chemical formula 15 was synthesized as follow.

First, tri(isopropyl)silylacetylene was reacted with commercially available 4'-brombenzo-18-crown 6-ether in the presence of $PdCl_2(PPh_3)_2$, copper iodide, and triethylamine at a reaction temperature of 80° C. Next, tetra butyl ammonium fluoride was reacted to the reactant for desilylation and the synthesis was thereby feasible.

The crown ether containing intramolecularly triazapentalenes represented by the chemical formula 16 was soluble in various organic solvents and water as well, and changes in fluorescence by addition of potassium ion were measured in an aqueous solution. The method for measurement will be specifically described below.

The crown ether containing intramolecularly triazapentalenes represented by the chemical formula 16 was made into an aqueous solution. Here, two samples with a concentration of the above compound of $1.84 \times 10^{-4}$ mol/L were prepared and one sample with a concentration of the above compound of $3.07 \times 10^{-4}$ mol/L was prepared. As the potassium ion, as represented by the chemical formula 17, potassium bromide (KBr) was added to make homogeneous solution (reaction formula (7)). The amount of potassium bromide added amount was 0 equivalents (when the sample with a concentration of crown ether compound containing triazapentalenes of $3.07 \times 10^{-4}$ mol/L was used), 10 equivalents (when the sample with a concentration of crown ether compound containing triazapentalenes of $1.84 \times 10^{-4}$ mol/L was used) and 100 equivalents (when the sample with a concentration of crown ether compound containing triazapentalenes of $1.84 \times 10^{-4}$ mol/L was used).

Using a fluorescence spectrophotometer (manufactured by Hitachi High-Technologies Corporation, F-4500), the ultraviolet absorption spectrum was measured, and the absorption maximum wavelength ($\lambda_{max}$) was determined to be 320 nm. The concentration of a sample solution was adjusted such that the intensity (Abs.) of absorption maximum wavelength was 0.100±0.005. Using a spectrophotometer (manufactured by Hitachi High-Technologies Corporation, U-3500), the fluorescence spectrum was measured with excitation wavelength ($\lambda_{ex}$)=320 nm.

Figure 3:
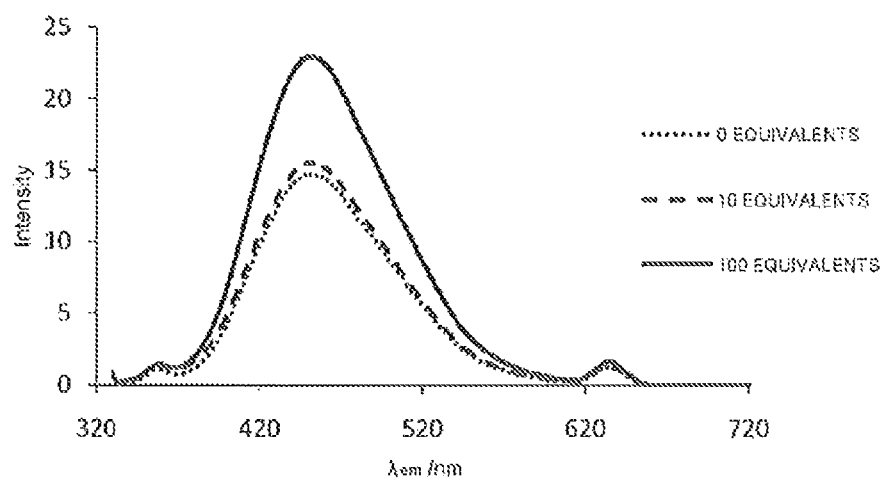
FIG. 3 is a graph chart showing the result of the example of the present invention.

As shown in a graph of FIG. 3, it was observed that, as the amount of KBr added increased, the fluorescence intensity became stronger. When 10 equivalents of KBr were added, an increase in the fluorescence intensity was observed, and when 100 equivalents thereof were added, a greater increase in the fluorescence intensity was observed. Because there was a proportional relationship between the amount of KBr added and the increase in fluorescence, the crown ether compound containing intramolecularly triazapentalenes according to the present example was found to be feasible for use as an ion concentration sensor.

(7)

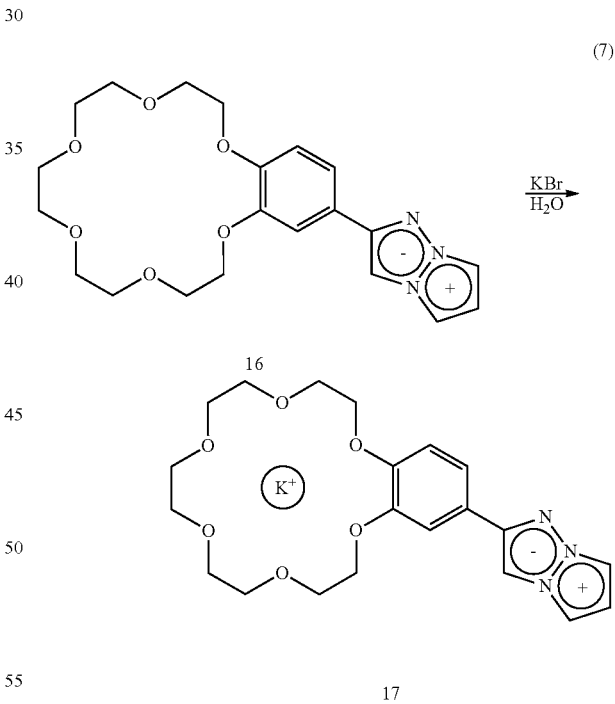

Example 6

For each of the compounds shown in Table 3, the maximum absorption wavelength ($\lambda_{abs}^{max}$), maximum fluorescence wavelength ($\lambda_{em}^{max}$), and fluorescence quantum yield ($\Phi_F$) were measured. Further, the Hammett constant ($\sigma_p$) of substituent group was together described in Table 3. In Table 3, "-" represents no measurement data available. The measurement of the absorption wavelength, fluorescence wavelength, and fluorescence quantum yield was carried out in the same manner as described in Example 3. Here, a method of synthesizing compounds of 1o$^a$ and 1r will be later described in Example 8. Compounds of 1e, 1n, 1f, 1g, 1l, 1k, 1h, and 1m, which are shown in Table 3 were synthesized by the method and condition described in Examples 1 to 2. Further, the compound 1a shown in Table 3 was synthesized under the under the same condition as in Example 1 and Example 2 except that a CO$_2$CH$_3$ part in the chemical formula 13 of the reaction formula (5) was replaced with a hydrogen atom. Thereby, the compound 1a having a triazapentalene backbone whose R$^5$ position was bound with the hydrogen atom was obtained.

compound having a triazapentalene backbone according to the present example had large difference between the maximum absorption wavelength and maximum fluorescence wavelength (Stokes shift).

Example 7

Synthesis of Disubstituted Product

Tetrahydrofuran (0.68 mL) was added to azide represented by the chemical formula 18 (20 mg, 0.068 mmol) contained in a 10-mL eggplant-shaped flask and stirred at room temperature to a homogeneous solution. To the solution, copper

TABLE 3

| 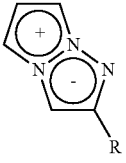 | 1a | 1e | 1o$^a$ | 1r | 1n | 1f |
|---|---|---|---|---|---|---|
| |  | 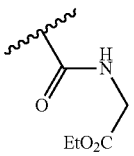 |  | 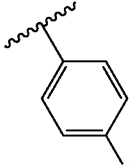 |  | 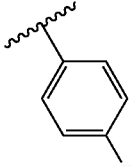 |
| $\lambda_{abs}^{max}$(nm) | — | 342 | 317 | 330 | 330 | — |
| $\lambda_{em}^{max}$(nm) | 389 | 431 | 449 | 418 | 413 | — |
| $\phi_F$ | 0.017 | 0.21 | 0.034 | 0.039 | 0.062 | — |
| Hammett $\sigma_P$ | — | — | — | — | −0.28 | 0.00 |

|  | 1g | 1l | 1k | 1h | 1m |
|---|---|---|---|---|---|
| | 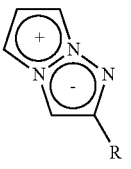 | 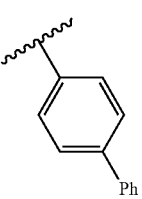 |  | 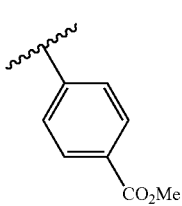 | 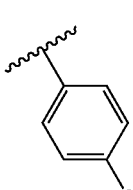 |
| $\lambda_{abs}^{max}$(nm) | 345 | — | 376 | 381 | 412 |
| $\lambda_{em}^{max}$(nm) | 456 | — | 510 | 509 | 556 |
| $\phi_F$ | 0.24 | — | 0.51 | 0.18 | 0.16 |
| Hammett $\sigma_P$ | 0.04 | 0.22 | 0.47 | 0.71 | 0.81 |

<Hammett Constant>

Figure 4:
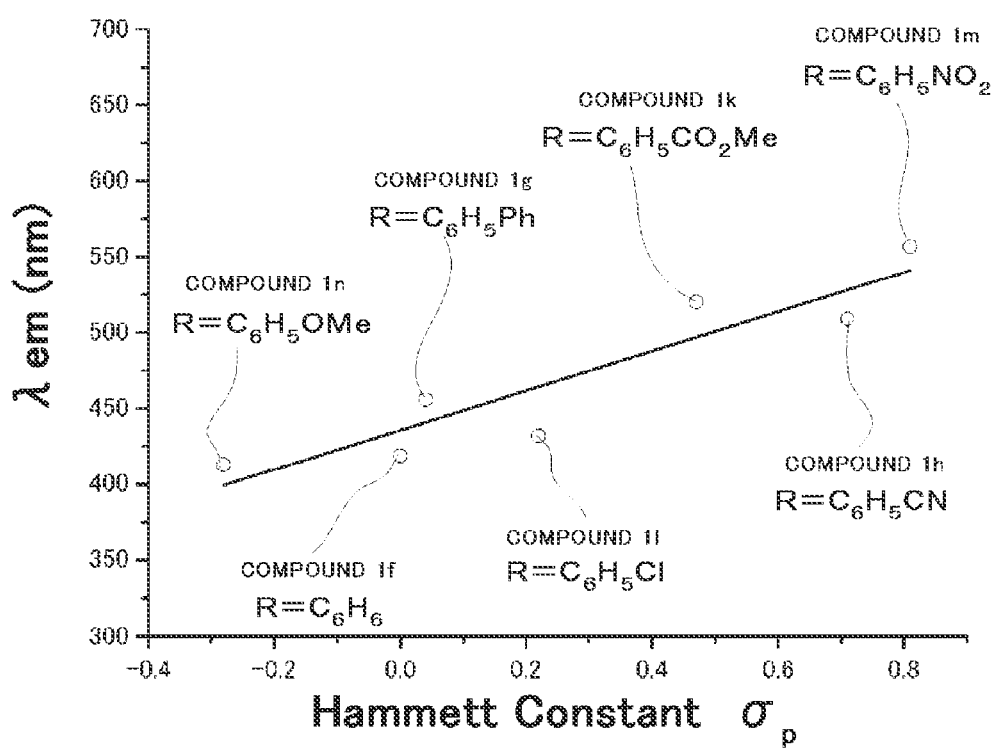
FIG. 4 is a graph chart showing the result of the example of the present invention.
Figure 5:
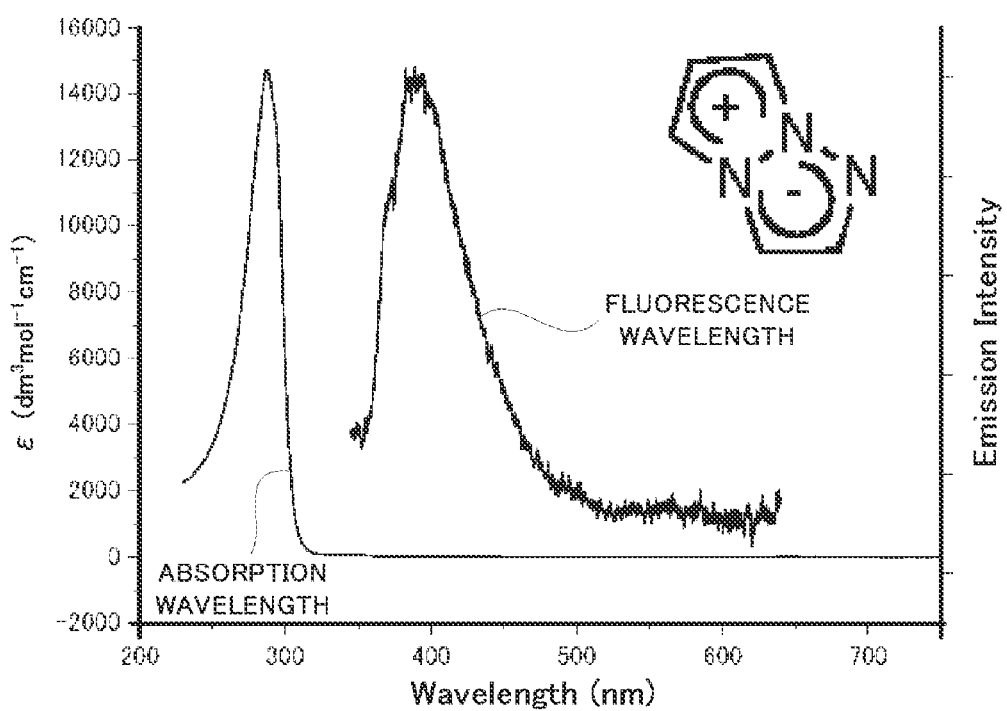
FIG. 5 is a graph chart showing the result of the example of the present invention.
Figure 6:
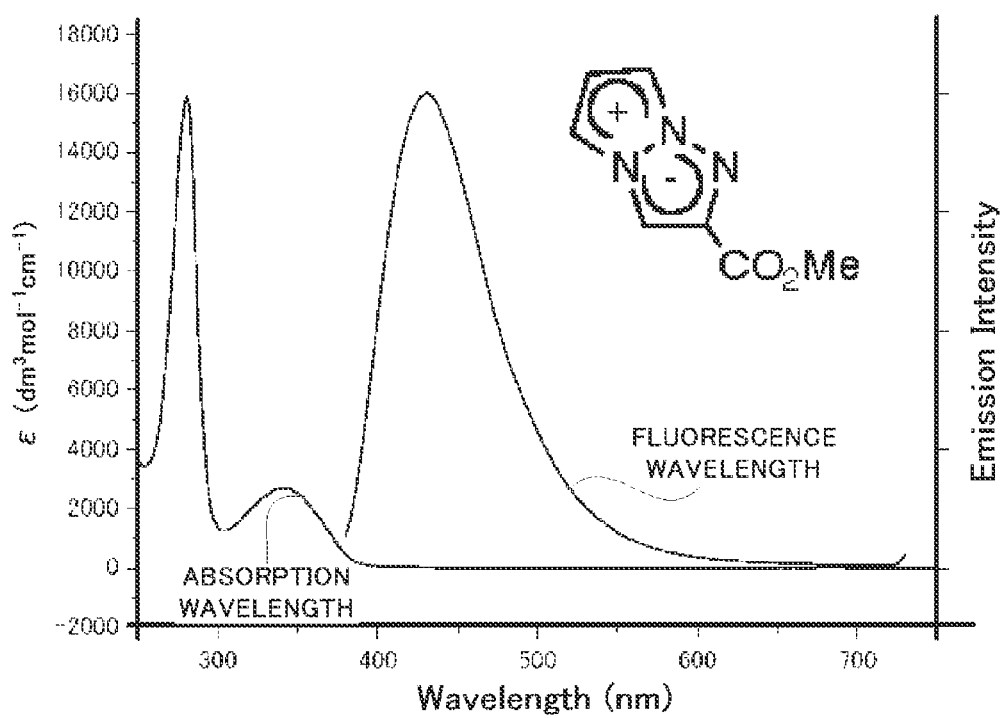
FIG. 6 is a graph chart showing the result of the example of the present invention.
Figure 7:
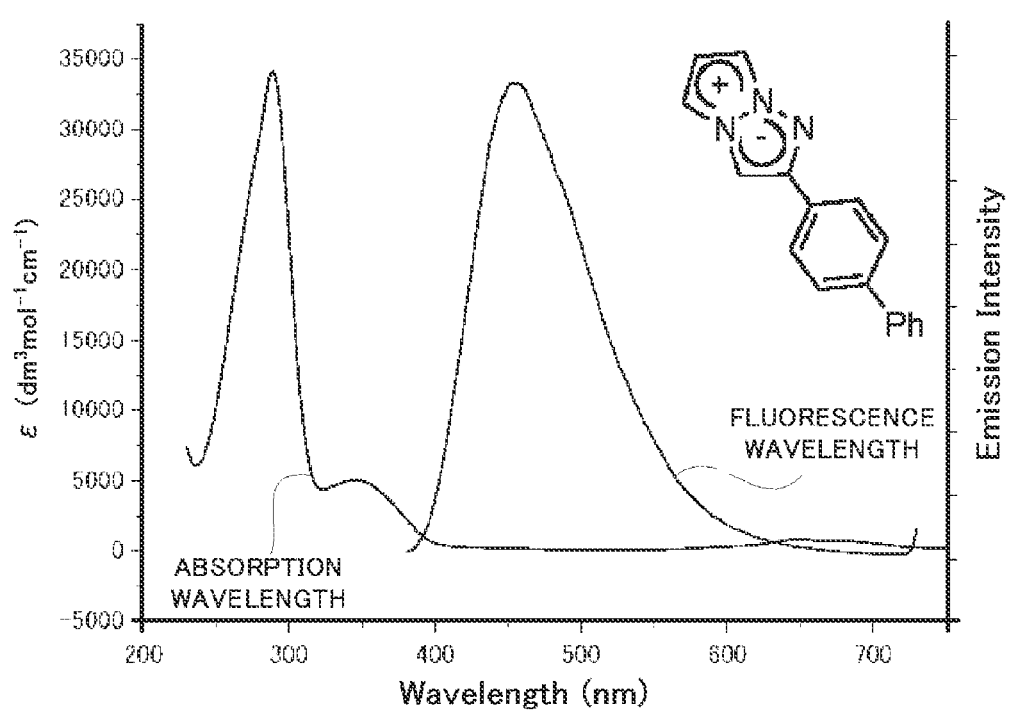
FIG. 7 is a graph chart showing the result of the example of the present invention.
Figure 8:
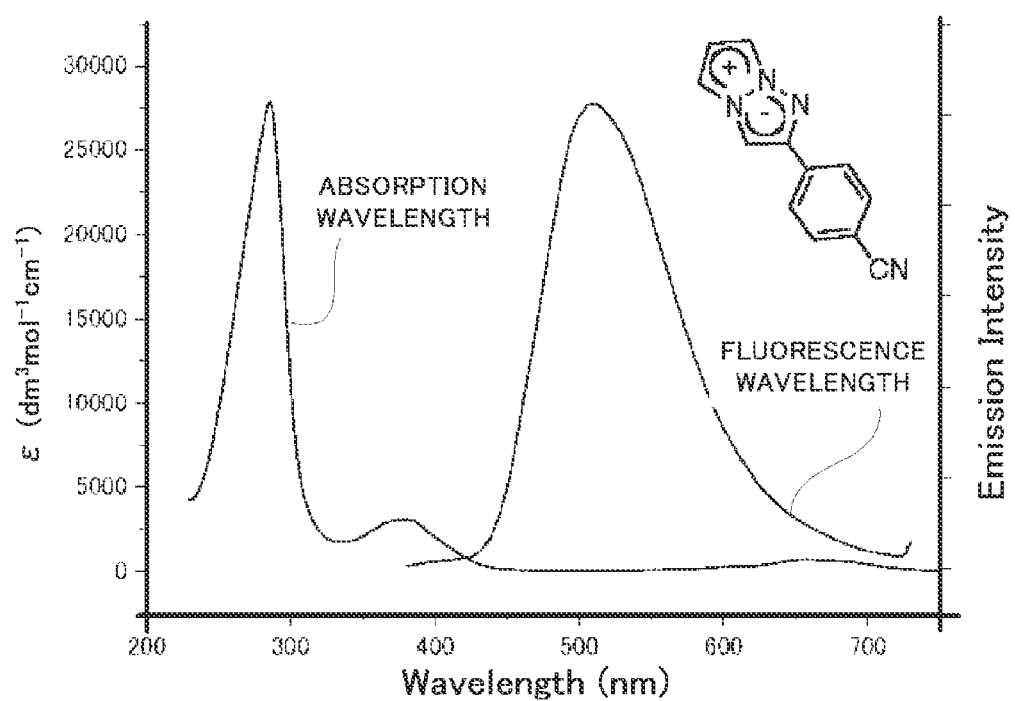
FIG. 8 is a graph chart showing the result of the example of the present invention.
Figure 9:
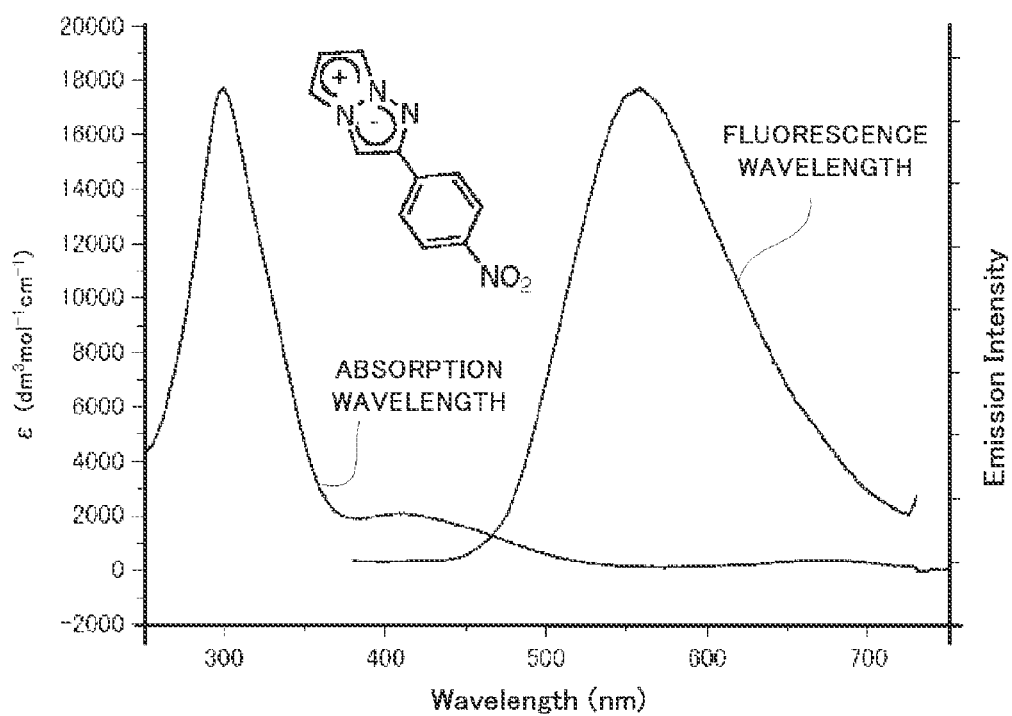
FIG. 9 is a graph chart showing the result of the example of the present invention.
Figure 10:
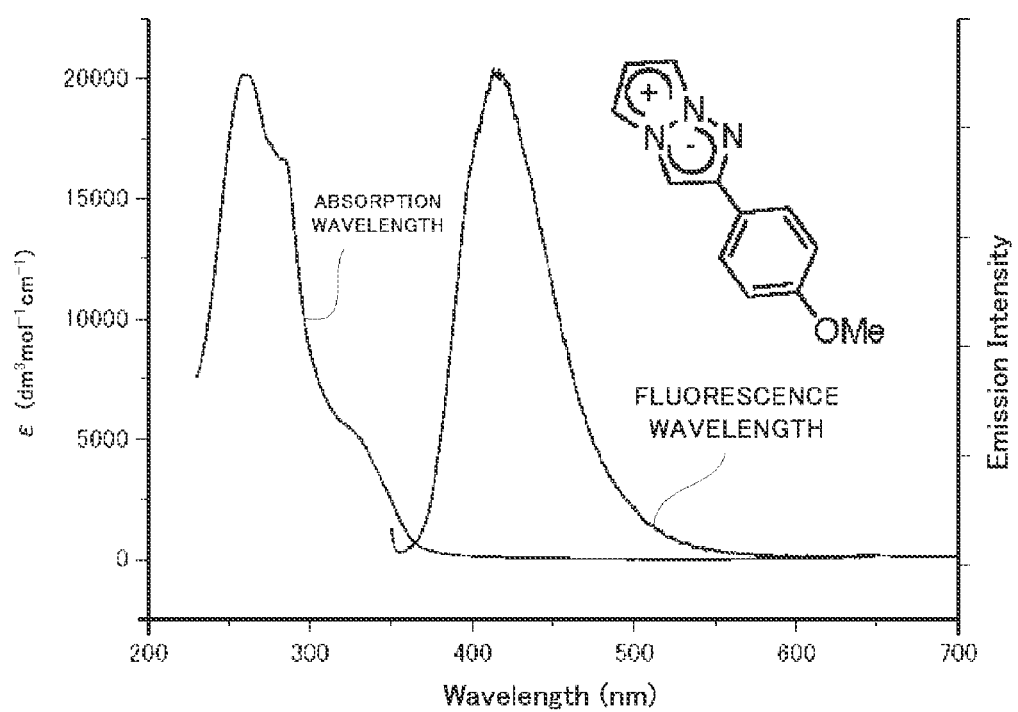
FIG. 10 is a graph chart showing the result of the example of the present invention.
Figure 11:
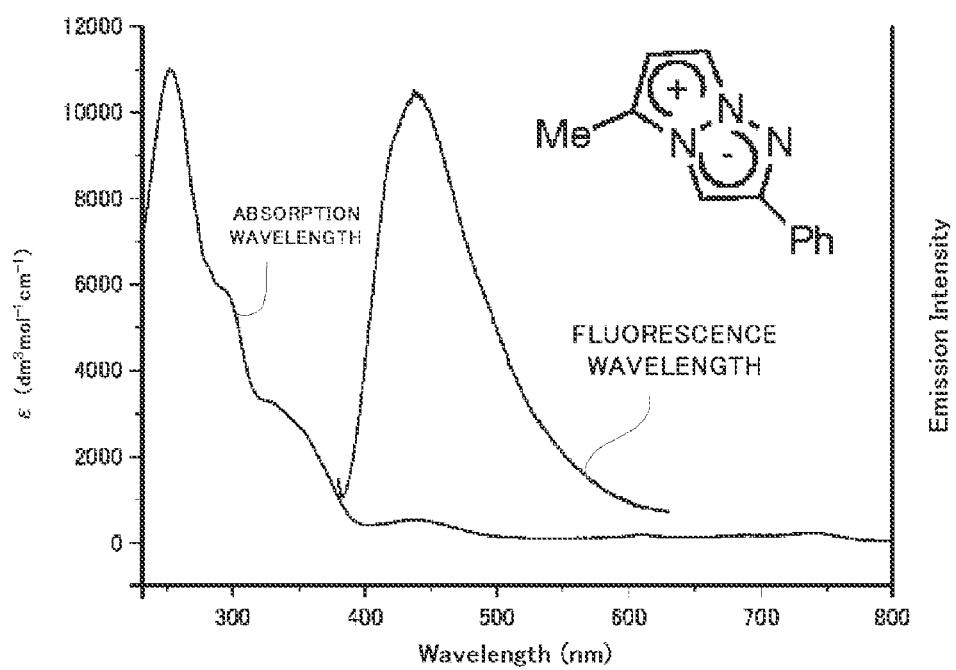
FIG. 11 is a graph chart showing the result of the example of the present invention.
Figure 12:
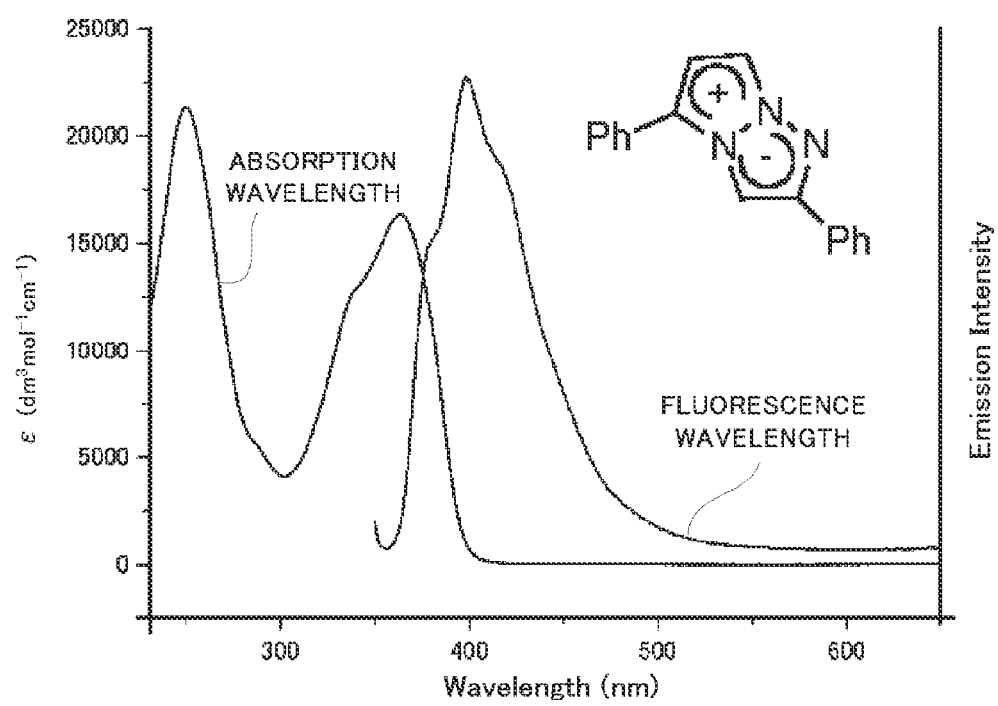
FIG. 12 is a graph chart showing the result of the example of the present invention.
Figure 13:
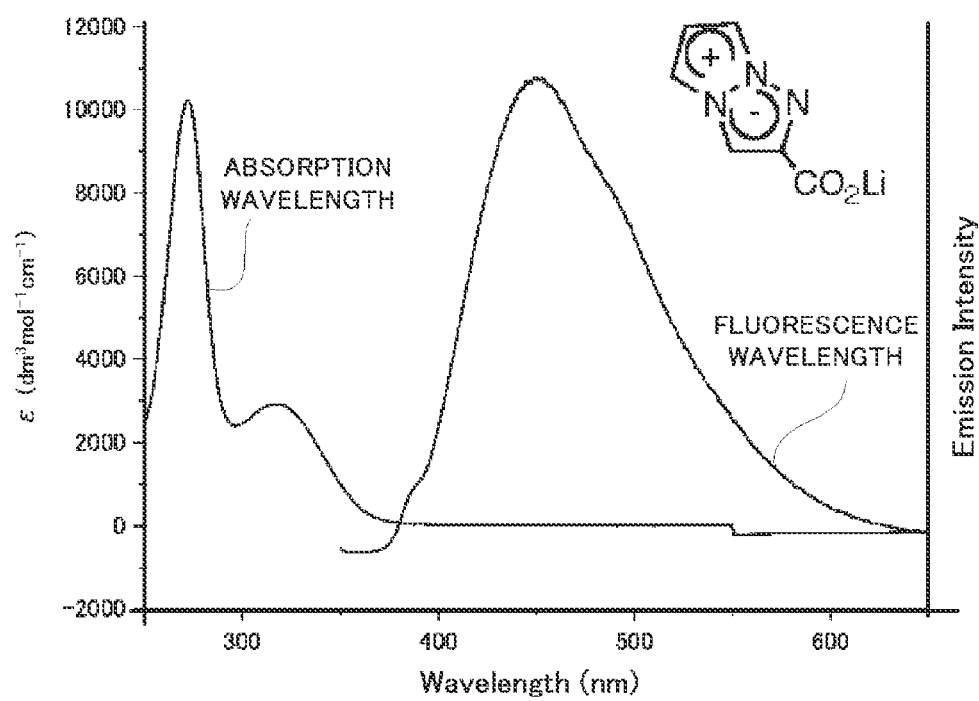
FIG. 13 is a graph chart showing the result of the example of the present invention.
Figure 14:
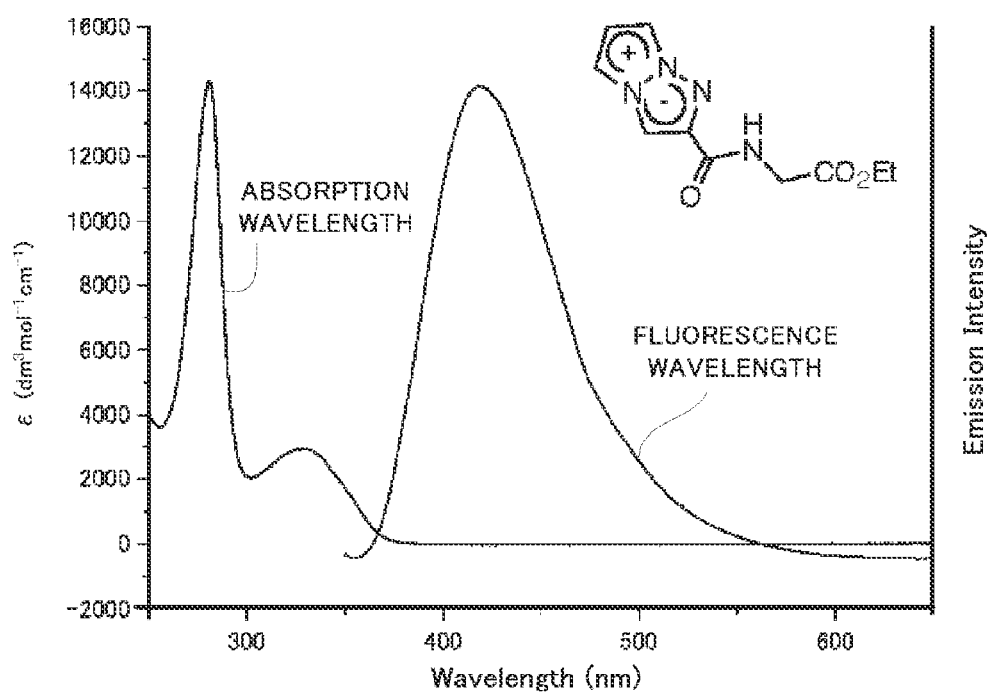
FIG. 14 is a graph chart showing the result of the example of the present invention.

FIG. 4 is a figure in which the Hammett constant and maximum fluorescence wavelength of each of the compounds of 1f, 1g, 1h, 1k, 1l, 1m and 1n which shown in Table 3 is plotted to show graphically. As shown in FIG. 4, it was found that the maximum fluorescence wavelength of the compound according to the present example tended to be a longer wavelength as the Hammett constant of the substituent group increased. Thus, it was found that changing the substituent group made it possible to regulate the fluorescent color.

<Stokes Shift>

For each of the compounds shown in Table 3, each fluorescence spectrum with the maximum absorption wavelength and maximum fluorescence wavelength is shown in FIG. 5 to FIG. 14. As shown in FIG. 5 to FIG. 14, it was found that the iodide•amino ether complex THF solution (341 mL, 0.034 mmol, 0.01M) prepared in advance and alkyne represented by the chemical formula 19 (8.7 mg, 0.068 mmol) were added in the order mentioned, and stirred at room temperature for 12 hours. With regard to the copper iodide•amino ether complex THF solution, copper iodide•amino ether complex solution (0.01M):copper iodide (19 mg, 0.01 mmol) and (Me$_2$NCH$_2$CH$_2$)$_2$O (19 mL, 0.01 mmol) were added to THF (10 mL), then subjected to sonication for one minute and then stirred at room temperature for 10 minutes, thereby obtaining the copper iodide•amino ether complex THF solution complex. Subsequently, the mixture was heated to reflux for additional 12 hours, then cooled to −78° C., added with KHMDS (0.55 mKL, 1 M THF solution), and stirred for 5 minutes. At −78° C., acetic acid was added thereto to terminate the reaction. The reaction solution was diluted with ether and an ether layer was washed with water. The ether layer was dried with anhydrous magnesium sulfate, filtered, and concentrated by a rotatory evaporator, thereby obtaining a crude product represented by the chemical formula 20. The concentrate was subjected to silica gel column chromatography purification (developing solvent=hexane/ethyl acetate=5/1 to 3/1), thereby obtaining a compound represented by the chemical formula 20 (9.7 mg, 60%) as a pale yellow solid (reaction formula (8)).

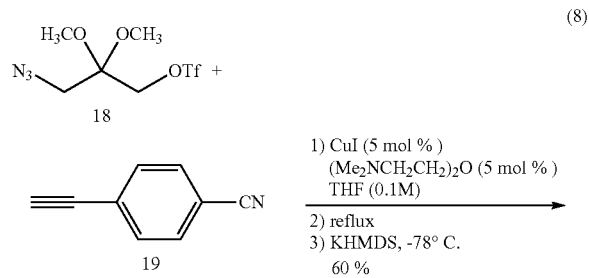

(8)

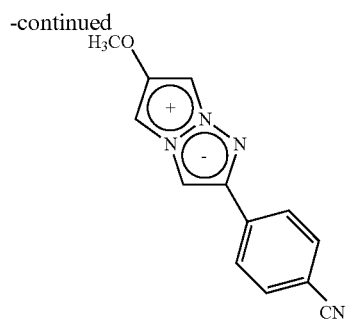

20

<Fluorescence of Disubstituted Product>

The absorption wavelength, fluorescence wavelength, and quantum yield of the disubstituted product are shown in Table 4 and Table 5. Disubstituted products other than the disubstituted product represented by the chemical formula 20 are synthesized by the same method as the disubstituted product represented by the chemical formula 20. The numerical values in Table 4 and Table 5 were obtained in $CH_2Cl_2$ solution under a condition of an excitation wavelength of 370 nm

TABLE 4

| | H | Me | MeO | NC |
|---|---|---|---|---|
| $\lambda_{abs}$(nm) | 381 | 385 | 378 | 360 |
| $\lambda_{em}$(nm) | 509 | 510 | 501 | 453 |
| $\phi_F$ | 0.18 | 0.55 | 0.57 | 0.46 |

TABLE 5

| | H | Me | Me |
|---|---|---|---|
| $\lambda_{abs}$(nm) | 381 | 385 | 388 |
| $\lambda_{em}$(nm) | 509 | 510 | 530 |
| $\phi_F$ | 0.18 | 0.55 | 0.21 |

As shown in Table 4 to Table 5, it was found that the quantum yield of a 2,5-substituted product with an electron donating group being $R^2$ and with an electron withdrawing group being $R^5$ was further larger than that of any other compounds and the fluorescence intensity of the 2,5-substituted product was further larger. Further, it was found that the fluorescence wavelength of a 2,5-substituted product with both $R^2$ and $R^5$ being electron withdrawing groups shifted to the short wavelength side, as compared with a 2,5-substituted product with only the position of $R^5$ being electron withdrawing group.

Example 8

Substitution with Functional Group Containing Hetero Atom

A compound having a triazapentalene backbone represented by the chemical formula 21 (57.1 mg, 0.35 mmol) was dissolved in methanol (1.3 mL) and water (0.4 mL) solvent, and the solution was added to LiOH.H$_2$O (14.5 mg, 0.35 mmol) at 0° C. The mixture was stirred at room temperature for 16 hours and concentrated under reduced pressure to obtain a lithium salt having a triazapentalene backbone represented by the chemical formula 22 as a red non-crystalline substance. The concentrate was dissolved in DMF (1.7 mL) and cooled to 0° C. To the mixture, EDCI (148 mg, 0.77 mmol), DMAP (14 mg, 0.11 mmol) and glycine ethyl ester hydrochloride (97 mg, 0.69 mmol) were added. The mixture was stirred at room temperature for 18 hours, then cooled together with a 5% citric acid aqueous solution (pH was 5 or less) and extracted with ethyl acetate (×2). The mixture organic layer was washed with salt water, dried with anhydrous magnesium sulfate, filtered, and concentrated under reduced pressure. The concentrate was purified by silica gel column chromatography purification (developing solvent=hexane/ethyl acetate=3/2) to obtain a compound having a triazapentalene backbone represented by the chemical formula 23 as a yellow crystal (42.1 mg, 0.178 mmol, 52%) (reaction formula (9)).

(9)

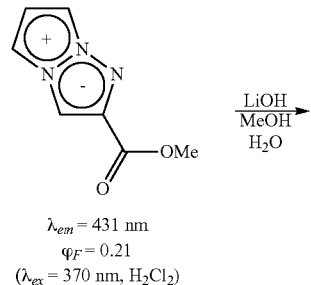

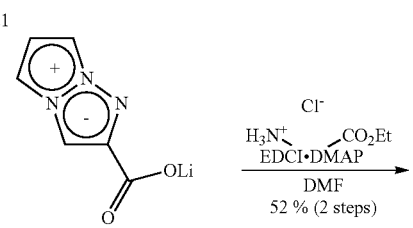

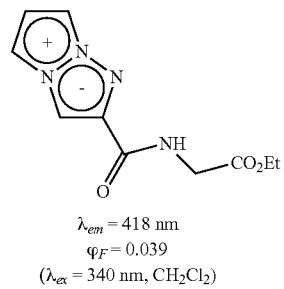

Compounds having triazapentalene backbones having substitutions with functional groups containing other hetero atoms are synthesized by the same method as the above-mentioned method. Further, it is possible to carry out the synthesis using a method of substituting the methyl ester group of compound having a triazapentalene backbone represented by the chemical formula 1k of Table 3 with acid chloride, or the like.

It was confirmed that the compound having a triazapentalene backbone represented by the chemical formula 23 that was synthesized in the present example also exhibited fluorescence (fluorescence wavelength: 418 nm) in an aqueous solution when irradiated in CH$_2$Cl$_2$ aqueous solution at an excitation wavelength of 340 nm.

It is noted that the present invention is not limited to the above examples and various variations and applications are allowed.

This application claims priority to Japanese Patent Application No. 2011-053009 filed on Mar. 10, 2011. The description, claims, and drawings are incorporated herein in their entirety by reference.

INDUSTRIAL APPLICABILITY

It is possible to utilize a compound having a triazapentalene backbone as a fluorescent chromophore according to the present invention in basic research and medical diagnosis for measurement of ion concentration inside living cells by utilizing as an ion concentration sensor. In addition, it is possible to utilize the compound as a reagent for water quality survey. Further, it is possible to utilize the compound as a reagent for chemical biology for searching for unknown protein as a fluorescent labeling group and for uncovering the in vivo localization of low molecular weight molecule compounds. Furthermore, because the compound emits fluorescence even in solid form, it is possible for the compound to be utilized as a luminescent material.

The invention claimed is:

1. A fluorescence agent comprising, as a fluorescent chromophore, a structure represented by the general formula 2:

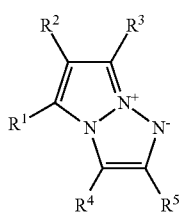

wherein $R^1$, $R^2$, $R^3$, $R^4$ and $R^5$, same or different, represent substituent groups;

wherein at least one substituent group of said $R^1$, $R^2$, $R^3$, $R^4$ and $R^5$ is an electron withdrawing group;

wherein said substituent group of $R^4$ and/or $R^5$ is an electron withdrawing group;

wherein two or more groups of $R^1$, $R^2$, $R^3$, $R^4$ and $R^5$ do not join together to form a ring; and wherein the structure of the general formula 2 is not 2-phenyl-1,3a,6a-triazapentalene.

2. The fluorescence agent according to claim 1 characterized in that said substituent group of $R^2$ is an electron donating group or an electron withdrawing group.

3. The fluorescence agent according to claim 1 comprising: a constituent unit represented by the general formula 3:

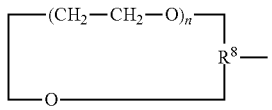

3 wherein n is integer from 3 to 5, and wherein $R^8$ is an alkylene group with two carbon atoms or more which may be branched, or an arylene group that may comprise a substituent group with six carbon atoms or more.

4. An ion concentration sensor comprising said fluorescence agent according to claim 1.

5. A reagent comprising said fluorescence agent according to claim 1.

6. A reagent kit comprising at least one of said reagents according to claim 5.

7. The reagent kit according to claim 6 characterized in that a maximum fluorescence wavelength of at least one of said reagent is a maximum fluorescence wavelength selected from the group consisting of 400 nm or more and 430 nm and less, more than 430 nm and 480 nm or less, more than 480 nm and 530 nm or less, and more than 530 nm and 2000 nm or less.

8. A method of synthesizing said fluorescence agent according to claim 1, comprising:

the step of subjecting an organic azide with a leaving group and an alkyne or a substituted alkyne to a dipolar cycloaddition reaction in the presence of a catalyst promoting said dipolar cycloaddition reaction.

9. The method of synthesizing a fluorescence agent according to claim 8, said method synthesizing a fluorescence agent comprising:

a structure represented by the general formula 2:

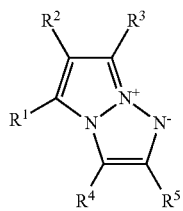

2 comprising subjecting said organic azide presented by the general formula 4:

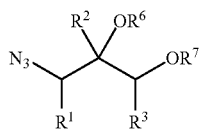

4 and said alkyne presented by the general formula 5:

5 or a substituted alkyne thereof to said dipolar cycloaddition reaction in the presence of a catalyst promoting said dipolar cycloaddition reaction wherein $R^6$ and $R^7$, same or different, represent substituent groups.

* * * * *